US008444683B2

(12) United States Patent
Mahadevan-Jansen et al.

(10) Patent No.: US 8,444,683 B2
(45) Date of Patent: May 21, 2013

(54) APPARATUS AND METHODS FOR OPTICAL STIMULATION OF NEURAL TISSUES

(75) Inventors: Anita Mahadevan-Jansen, Nashville, TN (US); Jonathon D. Wells, Seattle, WA (US); E. Duco Jansen, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 700 days.

(21) Appl. No.: 11/945,649

(22) Filed: Nov. 27, 2007

(65) Prior Publication Data

US 2009/0069871 A1    Mar. 12, 2009

Related U.S. Application Data

(60) Provisional application No. 60/861,673, filed on Nov. 27, 2006.

(51) Int. Cl.
*A61N 5/06* (2006.01)

(52) U.S. Cl.
USPC ............................................ 607/89; 128/898

(58) Field of Classification Search
None
See application file for complete search history.

(56) References Cited

U.S. PATENT DOCUMENTS

| | | | |
|---|---|---|---|
| 2003/0167080 A1* | 9/2003 | Hart et al. | 607/88 |
| 2004/0039378 A1* | 2/2004 | Lin | 606/6 |
| 2005/0216072 A1* | 9/2005 | Mahadevan-Jansen et al. | 607/89 |

OTHER PUBLICATIONS

Wells, J.D. et al., Application of Infrared Light for in vivo Neural Stimulation, Journal of Biomedical Optics, 2005, p. 064003, 10(6).
Jacques, S.L., Laser-tissue interactions, Photochemical, photothermal, and photomechanical, Surg. Clin. of North Am., 1992, 72(3), p. 531-58.
Chung, M.K. et al., Biphasic currents evoked by chemical or thermal activation of the heat-gated ion channel, TRPV3, J. of Biol. Chem., 2005, 280(16), p. 15928-41.
Orchardson, R., The generation of nerve impulses in mammalian axons by changing the concentrations of the normal constituents of extracellular fluid, J Physiol, 1978, 275, p. 177-89.
Quasthoff, S., A mechanosensitive K+ channel with fast-gating kinetics on human axons blocked by gadolinium ions, Neurosci. Lett., 1994, 169(1-2), p. 39-42.
Yamamoto, M. et al., Production of singlet oxygen on irradiation of a photodynamic therapy agent, zinc-coproporphyrin III, with low host toxicity, Biometals, 2003, 16(4), p. 591-7.
Takahashi, M. et al., Roles of reactive oxygen species in monocyte activation induced by photochemical reactions during photodynamic therapy, Front Med. Biol. Eng., 2002, 11(4), p. 279-94.

(Continued)

*Primary Examiner* — Bill Thomson
*Assistant Examiner* — Lynsey Crandall
(74) *Attorney, Agent, or Firm* — Morris, Manning & Martin, LLP; Tim Tingkang Xia, Esq.

(57) ABSTRACT

The present invention, in one aspect, relates to a method for stimulating neural tissue of a living subject. In one embodiment, the method has the steps of generating at least one beam of radiation; introducing at least one of one or more chromophores and one or more optical agents to a target neural tissue; and delivering the at least one beam of radiation to the target neural tissue, wherein the at least one beam of radiation is delivered with a radiant exposure that causes a thermal gradient in the target neural tissue, thereby stimulating the target neural tissue.

16 Claims, 10 Drawing Sheets

OTHER PUBLICATIONS

Ionita, M.A. et al., Photochemical and photodynamic properties of vitamin B2—riboflavin and liposomes, Oftalmologia, 2003, 58(3), p. 29-34. (Abstract Only).

Conlan, M.J. et al., Biostimulation of wound healing by low-energy laser irradiation, A review, J. Clin. Periodontol., 1996, 23(5), p. 492-6.

Walsh, L.J., The current status of low level laser therapy in dentistry. Part 1. Soft tissue applications, Aust. Dent. J., 1997, 42(4), p. 247-54.

Boulnois, J.L. et al, [Photo-biomolecular effects of laser radiation], Minerva Med., 1983, 74(27), p. 1669-73. (Abstract Only).

Doukas, A.G. et al., Biological effects of laser-induced shock waves: structural and functional cell damage in vitro, Ultrasound in Med. Biol., 1993, 19(2), p. 137-46.

Doukas, A.G. et al., Physical factors involved in stress-wave-induced cell injury: the effect of stress gradient. Ultrasound in Med. Biol., 1995, 21(7), p. 961-7.

Doukas, A.G. et al., Physical characteristics and biological effects of laser-induced stress waves, Ultrasound in Med. & Biol., 1996, 22(2), p. 151-64.

Jansen, E., Laser Tissue Interactions, 1st ed., Encylopedia of Biomaterials and Biomedical Engineering, 2004, Marcel Dekker Publishing, p. 883-891.

Thomsen, S., Pathologic analysis of photothermal and photomechanical effects of laser-tissue interactions, Photochem. and Photobiol., 1991, 53(6), p. 825-35.

Welch, A.J. et al., Optical-thermal response of laser-irradiated tissue, Lasers, photonics, and electro-optics, 1995, New York, Plenum Press, xxvi, 925p.

Telenkov, S.A. et al., Differential phase optical coherence probe for depth-resolved detection of photothermal response in tissue, Phys. Med. and Biol., 2004, 49(1), p. 111-9.

Rylander, C.G. et al., Quantitative phase-contrast imaging of cells with phase-sensitive optical coherence microscopy, Opt. Lett., 2004, 29(13), p. 1509-11.

Kim, J. et al., Optical coherence tomography speckle reduction by a partially spatially coherent source, J. of Biomed. Opt., 2005, 10(6), p. 064034.

Torres, J. H. et al., Limitations of a thermal camera in measuring surface temperature of laser-irradiated tissues, Lasers in Surg. and Med., 1990, 10(6), p. 510-23.

Waldman, G., Introduction to Light: The Physics of Light, Vision, and Color, 1983, Englewood Liffs, New Jersey, Prentice-Hall, Inc.

Niemz, M. H., Laser-Tissue Interactions, Fundamentals and Applications, 3rd Revised ed., 2004, Springer, 308.

Hill, B. C. et al., Laser interferometer measurement of changes in crayfish axon diameter concurrent with action potential, Science, 1977, 196(4288), p. 426-8.

Glickman, R. et al., Intracellular signaling mechanisms responsive to laser-induced photochemical and thermal stress, Proc. of SPIE, 2005, 5695, p. 260-269.

Hirase, H. et al., Multiphoton stimulation of neurons, J. Neurobiol., 2002, 51(3), p. 237-47.

Norton, S. J., Can ultrasound be used to stimulate nerve tissue? Biomed. Eng. Online, 2003, 2, p. 1-9.

Shusterman, V. et al., Direct mechanical stimulation of brainstem modulates cardiac rhythm and repolarization in humans, J. of Electrocardiol., 2002, 35 Suppl., p. 247-56.

Jansen, E. D. et al., Laser-tissue interaction during transmyocardial laser revascularization, Ann. Thorac. Surg., 1997, 63(3), p. 640-7.

Incropera, F. P. et al., Fundamentals of Heat and Mass Transfer, 5th ed., 2002, John Wiley and Sons, Inc.

Borrelli, M. J. et al., Sensitization to hyperthermia by 3,3'-dipentyloxacarbocyanine iodide: a positive correlation with DNA damage and negative correlations with altered cell morphology, oxygen consumption inhibition, and reduced ATP levels, Int. J. Hyperthermia, 1991, 7(2), p. 243-61.

Cole, A. et al., Ultrastructural study of mitochondrial damage in CHO cells exposed to hyperthermia, Radiat. Res., 1988, 115(3), p. 421-35.

Jacques, S. L. et al., Modeling optical and thermal distributions in tissue during laser irradiation, Lasers in Surg. Med., 1987, 6(6), p. 494-503.

Jacques, S. L. et al., Angular dependence of HeNe laser light scattering by human dermis, Lasers in the Life Sciences, 1987, 1(4), p. 309-334.

Kandel, E. R. et al., Principles of neural science, 4th ed., 2000, New York, McGraw-Hill, Health Professions Division, xli, 1414p.

Weiss, T. F., Cellular biophysics vol. 1: Transport, 1996, Cambridge, Mass, MIT Press.

Cesare, P. et al., Ion channels gated by heat, Proc. Natl. Acad. Sci. USA, 1999, 96(14), p. 7658-63.

Tominaga, M. et al., The cloned capsaicin receptor integrates multiple pain-producing stimuli, Neuron, 1998, 21(3), p. 531-43.

Nagy, I. et al., Noxious heat activates all capsaicin-sensitive and also a sub-population of capsaicin-insensitive dorsal root ganglion neurons, Neuroscience, 1999, 88(4), p. 995-7.

Cesare, P. et al., A novel heat-activated current in nociceptive neurons and its sensitization by bradykinin, Proc. Natl. Acad. Sci. USA, 1996. 93(26), p. 15435-9.

Benham, C. D. et al., TRPV channels as temperature sensors, Cell Calcium, 2003, 33(5-6), p. 479-87.

Liman, E. R., Thermal gating of TRP ion channels: food for thought? Sci. STKE, 2006, 2006(326), pe12.

Lyfenko, A. et al., The effects of excessive heat on heat-activated membrane currents in cultured dorsal root ganglia neurons from neonatal rat, Pain, 2002, 95(3), p. 207-14.

Van Der Stelt, M. et al., Endovanilloids, Putative endogenous ligands of transient receptor potential vanilloid 1 channels, Eur. J. Biochem., 2004, 271(10), p. 1827-34.

Hodgkin, A. L. et al., The effect of temperature on the electrical activity of the giant axon of the squid, J. Physiol., 1949, 109(1-2), p. 240-9.

Meyer, J. R. et al., Environmental modification of sciatic nerve conduction velocity in *Rana pipiens*, American Journal of Physiology, 1971, 220(5), p. 1383-7.

Thera P. Links et al., CA-tension relationships of muscle fibers from patients with periodic paralysis, Muscle & Nerve, 1993, 16(1), p. 109-117.

J. M. Khosrofian et al., Measurement of a Gaussian laser beam diameter through the direct inversion of knife-edge data, Applied Optics, 1983, 22(21), p. 3406-10.

Jonathon wells et al., Optical Stimulation of neural tissue in vivo, Optics Letters, 2005, 30(5), p. 504-506.

\* cited by examiner

APPARATUS AND METHODS FOR OPTICAL STIMULATION OF NEURAL TISSUES

CROSS-REFERENCE TO RELATED PATENT APPLICATION

This application claims the benefit, pursuant to 35 U.S.C. §19(e), of U.S. provisional patent application Ser. No. 60/861,673, filed Nov. 27, 2006, entitled "APPARATUS AND METHODS FOR OPTICAL STIMULATION OF NEURAL TISSUES," by Anita Mahadevan-Jansen, Jonathon D. Wells and E. Duco Jansen, which is incorporated herein by reference in its entirety.

Some references, which may include patents, patent applications and various publications, are cited in a reference list and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference. In terms of notation, hereinafter, "[2]" represents the nth reference cited in the reference list. For example, [2] represents the 2nd reference cited in the reference list, namely, Wells, J. D., Kao, C., Jansen, E. D., Konrad, P., Mahadevan-Jansen, A., *Application of Infrared Light for in vivo Neural Stimulation*. Journal of Biomedical Optics, 2005. 10: p. 064003.

STATEMENT AS TO RIGHTS UNDER FEDERALLY-SPONSORED RESEARCH

This invention was made with government support under Contract No. FA9550-04-1-0045 awarded by the United States Department of Defense and Contract No. R01 NS052407-01 awarded by the National Institute of Health. The government has certain rights in the invention.

FIELD OF THE INVENTION

The present invention relates generally to the stimulation of neural tissues, and more particularly to apparatus and methods for facilitation and/or enhancement of optical stimulation of neural tissues in vivo, with the use of at least one of one or more chromophores and one or more optical agents.

BACKGROUND OF THE INVENTION

For over a century, the traditional method of stimulating neural activity in humans during medical procedures has been based on electrical methods, which has undergone few modifications over the years and remains the gold standards to date. Electrical stimulation is utilized to identify the connectivity and functionality of specific nerve roots to be selectively avoided or resected as well as to create a unique map of functional structures that varies among individuals during brain tumor resection. However, electrical stimulation is prone to electrical interference from the environment, high frequency artifacts associated with the electrical signal used, intrinsic damage caused by the electrodes used for stimulation themselves, population response due to the recruitment of multiple axons, which prevents simultaneous stimulation and recording of adjacent areas, and in general poor spatial specificity.

Alternative approaches exist for stimulation of neural fibers (tissues) by optical irradiation. Researches on the excitability of neural tissue as a by-product of laser therapies and the capability of light in modulating its electrical conductivity have been reported [1, 2].

The use of lasers in medical procedures can be grouped into two distinct categories, therapeutic and diagnostic or imaging applications. In therapeutic procedures, the interaction between the laser and biological tissue results in a light distribution and absorption and subsequent photobiological effect that can be classified into, at least, three mechanistic categories, (1) photochemical, (2) photothermal, and (3) photomechanical [3]. Action potential propagation in neurons through chemical, thermal, and mechanical means [4-6] have been demonstrated. Photochemical effects depend on the absorption of light to act as a reagent in a stoichiometric reaction catalyzed by some photosensitizer. An example of a photochemical effect is the production of reactive chemicals (ultimately leading to oxygen radicals) reported in photodynamic therapy (PDT) by the combination of an injected extrinsic dye, singlet oxygen, and light [7-9]. Frequently, biostimulation is also attributed to photochemical interactions thought to target natural intrinsic agents, although this is not scientifically ascertained [10, 11]. Photothermal effects result from the transformation of absorbed light energy to heat, which may lead to hyperthermia, coagulation, or ablation of the target tissue [12]. Photomechanical effects are secondary to rapid heating with short laser pulses (<1 µs) that produce mechanical forces, such as explosive events and laser-induced pressure waves able to disturb cells and tissue [13, 14]. This classification of laser tissue interactions can be further separated into three distinct categories including; thermoelastic expansion, ablative recoil, and expansion secondary to phase change [15].

In the majority of therapeutic laser applications, the laser-tissue interaction is mediated by a thermal or thermo-mechanical process depending on the operational parameters of the laser, such as wavelength ($\lambda$), pulse duration ($\tau$), and laser radiant exposure or irradiance. In general, the objective is to damage tissue locally by exploiting high spatial precision and the ability to couple laser light into fiber optics for minimally invasive delivery to the tissue [16]. While optical nerve stimulation does exploit these distinctive delivery advantages, the therapeutic result for this technique is a stimulation effect in tissue rather than destruction. Laser radiant exposure ($J/cm^2$) associated with these procedures results in either reversible or non-reversible thermal or mechanical alterations of the tissue. The key parameter, wavelength, determines light distribution in the tissue dictated by wavelength dependent optical properties. The energy density and subsequent temperature rise resulting from absorption of optical energy is inversely proportional to the penetration depth and depending on the laser radiant exposure, a temperature increase is induced in the tissue (for comprehensive review see: [17]). While photochemical processes are often governed by a specific reaction pathway, photothermal effects are non-specific and are mediated by absorption of optical energy and secondly governed by fundamental principles of heat transport. Subsequent effects in the target tissue are determined by the temperature rise and the duration of the temperature exposure as described by an Arrhenius rate process [18].

It is important to point out that the duration of the laser exposure, which is largely similar to the interaction time itself, distinguishes and primarily controls these photobiological processes. According to a graph of the laser radiant exposure versus the duration of pulse width the time scale can roughly be divided in three major sections [3]; continuous wave or exposure times >1 s for photochemical interactions, 100 s down to 1 µs for photothermal interactions, and 1 µs and shorter for photomechanical interactions, as shown in FIG. 10. These boundaries are not strict and adjacent interaction types cannot always be separated. For example, in the range of 1 μs to several hundreds of μs, the interaction mechanism has photothermal as well as photomechanical components, while many photochemical interactions also exhibit photothermal components.

Great clinical relevance would be gained if optimal laser parameters for safe and effective stimulation of nerves could be determined from the laser-tissue interactions that occur during optical nerve stimulation in clinical implementations. Understanding the biophysical mechanism will ultimately help to refine an optimal laser parameter set to effectively target the diverse morphology of neural tissue types as well as identify possible clinical applications and limitations for this nerve stimulation modality.

Therefore, a heretofore unaddressed need exists in the art to address the aforementioned deficiencies and inadequacies.

SUMMARY OF THE INVENTION

The present invention, among other things, discloses methods and systems for facilitation and/or enhancement of optical stimulation of neural tissues, with the use of exogenous chromophores, endogenous chromophores and/or optical agents. The exogenous agents may be external to the neurons and/or be loaded into the intracellular space, so long as the agents act to enhance the underlying mechanism of optical stimulation through a thermally mediated process and/or directly facilitate this optical stimulation of neural tissue using a chromophore normally not present in tissue to directly cause the thermally mediated mechanism by which pulsed laser stimulation occurs. Similarly, endogenous chromophores can be targeted near the cell membrane to cause efficient stimulation without significant absorption (i.e., heat generation) from surrounding tissues.

Generally, wavelengths of light for efficiently optical stimulation of tissues are determined by the tissue absorption spectrum, i.e., the intrinsic tissue absorption properties are primarily responsible for efficient stimulation with minimal tissue damage. The mechanism of action for this phenomenon is related to establishing a thermal gradient in the tissue at the level of the neuronal cell membrane that causes subsequent stimulation due to the increase in temperature. Furthermore, with the addition of exogenous/endogenous chromophores and/or optical agents in the target tissue, the absorption can be changed based on the material properties of that deposited enhancer. These properties may be optimized to not only absorb light efficiently (thus establish the thermal gradient in tissue) at the appropriate energy levels, but also act as a heat sync to minimize thermal damage in tissue associated with this nerve stimulation phenomenon. With the thermal mechanism for stimulation of neural tissue, any wavelength of light can be used for stimulation, provided the light is absorbed by the optical enhancing medium and transferred to heat locally near the cell membrane. An optimal wavelength for use of an exogenous/endogenous chromophore and/or optical agent is one that has minimal absorption in neural tissue, yet optimal absorption (i.e. absorption that is higher than that of the tissue) in the enhancing material, and one that localizes the thermal gradient near the cell membrane without significant absorption from other tissue layers.

The method according to the present invention has advantages over the existing optical neural stimulation methodology by: 1) increasing spatial resolution to only the area where exogenous chromophore is loaded or placed, 2) increasing the number of lasers and wavelengths available for optical stimulation by changing the absorption properties of the target tissue (thus allowing stimulation), 3) enhancing existing optimal wavelengths to decrease the amount of laser energy required for stimulation as well as possibly increasing the energy required for tissue damage by acting as a heat sync in the nerve, 4) allowing the possibility of non-invasive stimulation by coating/loading the target neurons prior to stimulation and the use of a laser with a wavelength that is both capable of penetrating soft tissue as well as being highly absorbed by the input chromophore.

In one aspect, the present invention relates to a method of optically stimulating a neural tissue of a living subject. In one embodiment, the method includes the steps of generating at least one beam of radiation; introducing at least one of one or more chromophores and one or more optical agents to a target neural tissue; and delivering the at least one beam of radiation to the target neural tissue, wherein the at least one beam of radiation is delivered with a radiant exposure that causes a thermal gradient in the target neural tissue, thereby stimulating the target neural tissue.

In one embodiment, the at least one of one or more chromophores and one or more optical agents are introduced to the intracellular space of the target neural tissue. In another embodiment, the at least one of one or more chromophores and one or more optical agents is introduced externally to the neurons of the target neural tissue.

The at least one beam of radiation has an intensity between a first intensity threshold and a second intensity threshold that is greater than the first intensity threshold, wherein the first intensity threshold is a stimulation threshold of the target tissue, and wherein the second intensity threshold is an ablation threshold of the target tissue. The ratio of the second intensity threshold to the first intensity threshold is a function of a wavelength of the at least one beam of radiation. In one embodiment, the ratio of the second intensity threshold to the first intensity threshold is in a range from 1 to 200, preferably in a range from 4 to 6. The at least one beam of radiation is delivered to the target neural tissue with the radiant exposure no more than 5.0 J/cm$^2$, preferably no more than 2.0 J/cm$^2$.

In one embodiment, the at least one beam of radiation has a wavelength selected such that when delivered to the target neural tissue, it causes a maximal temperature increase and a minimal tissue damage in the target neural tissue.

In one embodiment, the target neural tissue is characterized with a thermal diffusion time, $T_d$, and wherein the at least one beam of radiation comprises a plurality of pulses with a pulse duration, $T_p$, such that $T_p < T_d$.

In another aspect, the present invention relates to a method of optically stimulating a neural tissue of a living subject. In one embodiment, the method comprises the step of introducing at least one of one or more chromophores and one or more optical agents to a target neural tissue; and exposing the target neural tissue to a beam of radiation with a radiant exposure for an amount of time sufficient to establish a thermal gradient therein, thereby stimulating the target neural tissue, wherein the beam of radiation has an intensity between a stimulation threshold of the target neural tissue and an ablation threshold of the target neural tissue that is greater than the stimulation threshold of the target neural tissue.

The beam of radiation has a wavelength selected such that when delivered to the target neural tissue, it causes a maximal temperature increase and a minimal tissue damage in the target neural tissue.

The target neural tissue is characterized with a thermal diffusion time, $T_d$, and wherein the beam of radiation comprises a plurality of pulses with a pulse duration, $T_p$, such that $T_p < T_d$.

In yet another aspect, the present invention relates to a method of optically stimulating a neural tissue of a living subject. The neural tissue of interest is characterized with a thermal diffusion time, $T_d$. In one embodiment, the method has the step of delivering optical energy to a target neural tissues in pulses with a pulse duration $T_p$ such that $T_p<T_d$, and wherein the optical energy is delivered with a radiant exposure that causes a thermal gradient in the target neural tissue, thereby stimulating the target neural tissue. The method further has the step of introducing at least one of one or more chromophores and one or more optical agents to a target neural tissue prior to the delivering step. The target neural tissue receives the optical energy for an amount of time sufficient to initiate action potential propagation within the target neural tissue.

In one embodiment, the delivering step includes the step of focusing the optical energy on the target neural tissue so that the target neural tissue propagates an electrical impulse.

In a further aspect, the present invention relates to an apparatus for stimulating a neural tissue of a living subject, where the neural tissue is characterized with a thermal diffusion time, $T_d$. In one embodiment, the apparatus has an energy source for generating optical energy; and a delivering means coupled to the energy source for delivering the generated optical energy to the target neural tissue. The delivering means is configured to deliver the generated optical energy with a radiant exposure that causes a thermal gradient in the target neural tissue, thereby stimulating the target neural tissue, and the optical energy is delivered in pulses with a pulse duration $T_p$ such that $T_p<T_d$.

The apparatus further has a controlling means operably coupled to the energy source and the delivering means and the target neural tissue. In one embodiment, the controlling means includes a first detector operably coupled to the energy source for measuring the optical energy generated from the energy source; a second detector operably coupled to the target neural tissue for measuring the thermal gradient in the target neural tissue; and a computer operably coupled to the first detector and the second detector for evaluating the optical stimulation of the target neural tissue.

In one embodiment, the delivering means includes a connector having a body portion defining a channel extending from a first end to a second end; one or more optical fibers housed in the channel for transmitting the optical energy; and a probe operably coupled to the second end of the connector and having an end portion for delivering the optical energy to a target neural tissue. The delivering means may further include a selecting device operably coupled to the connector for selectively delivering the optical energy through at least one of the one or more optical fibers. Additionally, the delivering means may also include a movable stage that is operably coupled to the probe such that the probe is movable with the movable stage three-dimensionally to selectively deliver the optical energy to one or more neural fibers of the target neural tissue.

In another embodiment, the delivering means has a first optical means for directing the optical energy to a desired direction; and a second optical means for focusing the optical energy directed by the first optical means to a target neural tissue. The first optical means and the second optical means are positioned such that the energy source, the delivering means and the target neural tissue are positioned along an optical path. Each of the first optical means and the second optical means comprises at least one of one or more optical mirrors, one or more optical lenses, one or more optical couplers, and one or more optical fibers.

In one embodiment, the energy source has a laser capable of generating a beam of optical energy having a wavelength that is fixed or tunable. The laser includes a pulsed infrared laser, such as a free electron laser, an Alexandrite laser, a solid state laser, a $CO_2$ laser, a tunable optical parametric oscillator (OPO) laser system, an $N_2$ laser, an excimer laser, a Holmium-doped:Yttrium Aluminum Garnet (Ho:YAG) laser, or an Erbium doped:Yttrium Aluminum Garnet (Er:YAG) laser.

These and other aspects of the present invention will become apparent from the following description of the preferred embodiment taken in conjunction with the following drawings, although variations and modifications therein may be affected without departing from the spirit and scope of the novel concepts of the disclosure.

DETAILED DESCRIPTION OF THE INVENTION

Figure 1:
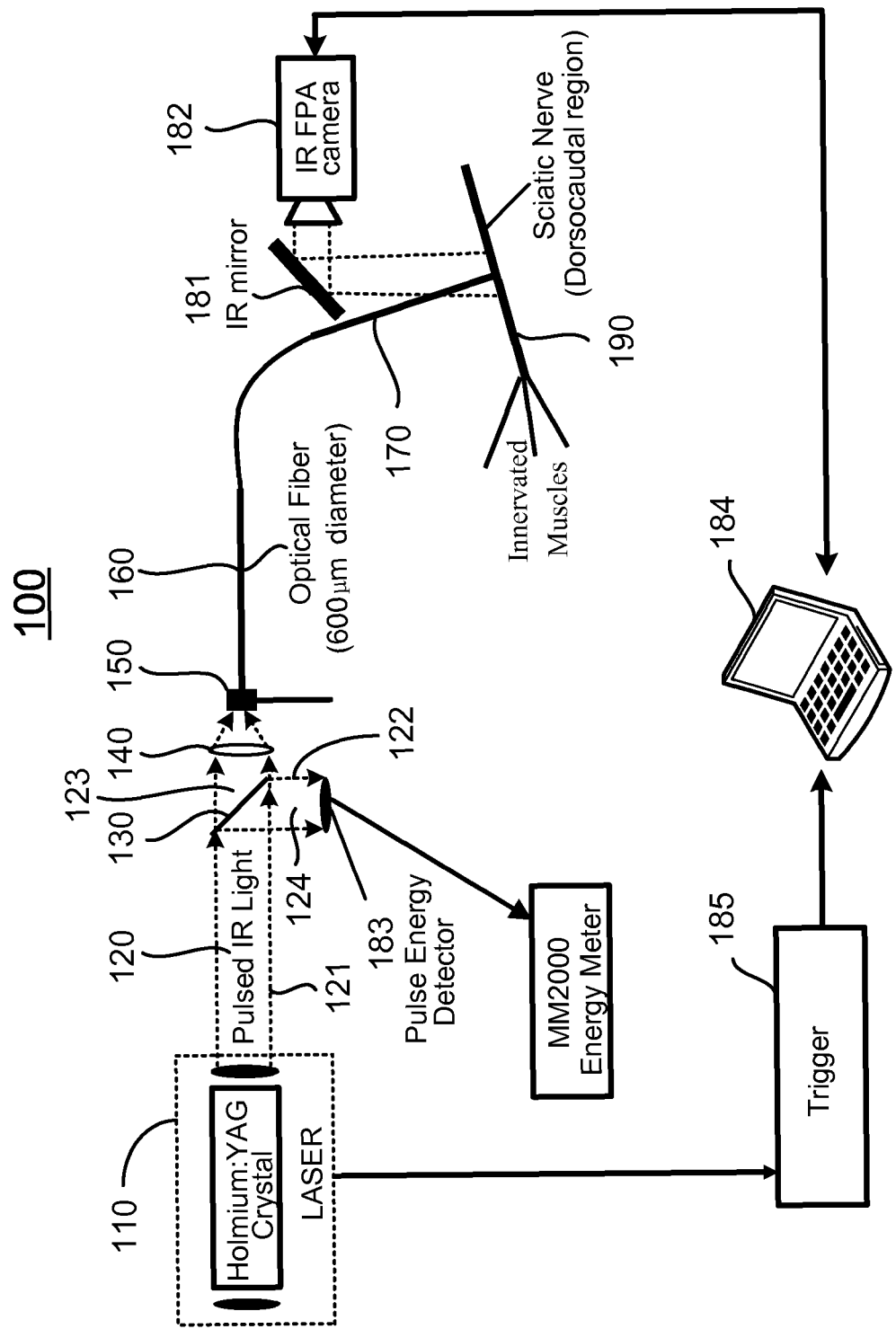
FIG. 1 shows schematically an experimental setup for nerve surface temperature measurements with a IR (thermal) camera according to one embodiment of the present invention.

The present invention is more particularly described in the following examples that are intended as illustrative only since numerous modifications and variations therein will be apparent to those skilled in the art. Various embodiments of the invention are now described in detail. Referring to the drawings, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present invention. Additionally, some terms used in this specification are more specifically defined below.

DEFINITIONS

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, the term "living subject" refers to a human being such as a patient, or an animal such as a lab testing rat, monkey or the like.

CNAP is an abbreviation for compound nerve action potential.

CMAP is an abbreviation for compound muscle action potential.

As used herein "target neural tissue" is defined as any neural tissue including, but not limited to, the sciatic nerve of the leopard frog (*Rana Pepieis*), the sciatic nerve of mammals, and brain and spinal cord tissue of mammals.

As used herein "electrical impulse" is defined an electrical current applied via electrodes on the nerve to initiate an action potential in the neuron.

As used herein "stimulation effect" is defined as propagation of an electrical signal within neural or muscular tissue.

As used herein "nerve fiber" is defined as a portion of the neuron, namely the axon, which carries action potentials from one end of the neuron to the other. Many nerve fibers compose a peripheral nerve, such as the sciatic nerve of a leopard frog (*Rana Pepiens*) or a mammal.

Northern Leopard Frog (*Rana Pepiens*) Sciatic Nerve Model System:

Leopard frogs (*Rana Pepiens*) provide a widely accepted model system for studying the stimulation of a neural tissue. The frog sciatic nerve provides a robust nerve preparation not susceptible to ischemic changes. Additionally, frogs have a neuromuscular innervation similar to mammals, and extensive research has been carried out by the research community on the ability of neurons to conduct an electrical impulse [48]. Finally, leopard frogs (*Rana Pepiens*) provide a model system that is capable of withstanding temperature and humidity variations [49].

Northern leopard frogs (*Rana Pepiens*) of sizes varying from 3-4 inches are selected so that the sciatic nerve may serve as the target neural tissue. The frogs are pithed so as to euthanize the animal. The frog is pithed to make it brain dead, while still maintaining the vital body functions and the nerve conduction. Subsequent to being pithed, the animal is immobilized on a wax bed. The skin covering the hamstring muscle is cut in order to expose the muscle. Subsequently, an incision is made along the length of the hamstring muscle so as to expose the sciatic nerve. The sciatic nerve is freed from the connective tissue that connected it to the surrounding muscle. For experimental purposes, several pairs of electrodes were placed on the nerve. The first pair of electrodes is capable of electrical stimulation, the second pair of electrodes is capable of recording the nerve potentials, and the third pair of electrodes was pierced into the muscle that the sciatic nerve innervates so that muscle potentials may be recorded. Additionally, the sciatic nerve was kept moist at all times by using saline water.

The methods described herein may have been used to stimulate a rat sciatic nerve. One of ordinary skill in the art understands the differences in the surgical procedure necessary to expose the rat sciatic nerve compared to the surgical procedure described above for the frog. The same method of optical stimulation was used for the rat nerve and frog nerve. Regarding the stimulation of the rat sciatic nerve, a wavelength of 4.4 micrometers, and energy of 4.7 mJ, a spot size of 619 micrometers, and a pulse frequency of 2 Hz using the FEL were used. Optical stimulation was also tested using an energy of 39 mJ, 1.78 mJ, or 2.39 mJ.

Free Electron Laser (FEL):

A free electron laser and delivery optics are used to generate and manipulate the optical energy. The optical energy transport system is maintained under rough vacuum. The optical energy is focused on the target neural tissue using focusing lenses (Vi Convex Lenses, f=300 mm) to a spot size of around 400 micrometers.

The response of the sciatic nerve to the optical energy stimulation is sensed using stainless steel needle electrodes that are placed under the sciatic nerve for compound nerve action potential recording. Additionally, the electrical response from the sciatic nerve is monitored by recording electrodes placed in the nerve downstream and innervated hamstring muscle. If the sciatic nerve conducts an electrical impulse, a tiny electrical signal can be detected from the nerve (CNAP) and a much larger electrical signal can be detected from the muscle (CMAP). The signals are recorded using the MP100 system from Biopac Systems (Santa Barbara, Calif.) that is combined electrical stimulation and recording unit. The nerve was electrically stimulated using S44 Grass electrical stimulator from Grass Instruments, Quincy, Mass.

Optical stimulation was performed using laser pulses with energy in the range from 0.2 mJ to 5 mJ with a spot size of 300-600 micrometers (fluence values varied from 0.2 J/cm$^2$ to about 10 J/cm$^2$). The minimum energy and therefore fluence required to stimulate the frog nerve was found to be minimum (0.6 J/cm$^2$) between 4 and 4.5 micrometers. The spot size of the optical energy was determined using the knife-edge method [50]. The laser pulses were focused onto the sciatic nerve using Biconvex Lenses. The laser pulse energy was varied using a polarizer. The information recorded on the MP100 system was displayed using the AcqKnowledge software.

The FEL was selected for use in the initial studies with this method since it has the following advantages. The FEL is tunable in wavelength from 2 to 10 micrometers. Thus, FEL offers the flexibility of providing various wavelengths in the infrared spectrum for use with the method provided herein. Other sources may be used to generate the necessary wavelength. In addition to any source that can generate wavelengths in the infrared portion of the spectrum, sources may include LED and LCD. FEL additionally provides micropulses, each about 1 picosecond in duration and having a repetition rate of about 3 GHz. The envelope of this pulse train forms a macropulse that is about 3-6 microseconds and can be delivered at a rate up to 30 Hz. As mentioned above, optical stimulation of the peripheral nerves employ pulse energies ranging from 0.2 mJ to 5 mJ in a spot size of around 500 micrometers.

Stimulation studies can also be performed using other sources such as a YAG laser for wavelengths in the UV, visible and infrared. Additionally, if it is desired to use a wavelength around 4 micrometers, then a lead-salt laser, or an optical parametric oscillator (or amplifier) may be used.

Overview of the Invention

Recently, it has been demonstrated by the inventors a fundamentally novel device for neural activation using low-level, pulsed infrared laser energy in vivo with resulting compound nerve and muscle potentials and associated muscle contraction. It is also shown that infrared laser light incorporated into a stimulation device at 4.0 and 2.1 µm can be used to consistently and reproducibly stimulate peripheral nerves in frogs and rats with no appreciable tissue damage using radiant exposures, laser energy per unit area, of 1.01 and 0.32 J/cm$^2$, respectively; 4-6 times below an ablation (damage) threshold. The ratio of the ablation threshold to a stimulation threshold (safety ratio) is found to be inversely proportional to the tissue absorption and this ratio is highest at relative valleys of tissue absorption in the infrared. Histological analysis shows no discernable tissue damage with chronic stimulation. These results prove that optical stimulation can circumvent many of the limitations of electrical stimulation, including lack of spatial specificity and electrical artifacts. The resulting nerve and muscle action potentials recorded are analogous to that observed with electrical stimulation. The pulsed, laser irradiation from a laser device can be focused to a small diffraction limited spot with a high degree of precision, thereby targeting specific neural fibers and facilitating spatial selectivity of neural response that is not attainable with electrical stimulation in vivo.

The present invention, among other things, discloses methods and systems for facilitation and/or enhancement of the optical stimulation of neural tissues, with the use of exogenous chromophores, endogenous chromophores and/or optical agents. In one embodiment, the method includes the steps of generating at least one beam of radiation; introducing at least one of one or more chromophores and one or more optical agents to a target neural tissue; and delivering the at least one beam of radiation to the target neural tissue, where the at least one beam of radiation is delivered with a radiant exposure that causes a thermal gradient in the target neural tissue, thereby stimulating the target neural tissue. The exogenous agents may be external to the neurons and/or be loaded into the intracellular space, so long as the agents act to enhance the underlying mechanism of optical stimulation through a thermally mediated process and/or directly facilitate this optical stimulation of neural tissue using a chromophore normally not present in tissue to directly cause the thermally mediated mechanism by which pulsed laser stimulation occurs. Similarly, endogenous chromophores can be targeted near the cell membrane to cause efficient stimulation without significant absorption (i.e., heat generation) from surrounding tissues.

The at least one beam of radiation has an intensity between a first intensity threshold and a second intensity threshold that is greater than the first intensity threshold, wherein the first intensity threshold is a stimulation threshold of the target tissue, and wherein the second intensity threshold is an ablation threshold of the target tissue. The ratio of the second intensity threshold to the first intensity threshold is a function of a wavelength of the at least one beam of radiation. In one embodiment, the ratio of the second intensity threshold to the first intensity threshold is in a range from 1 to 200, preferably in a range from 4 to 6. The at least one beam of radiation is delivered to the target neural tissue with the radiant exposure no more than 5.0 J/cm$^2$, preferably no more than 2.0 J/cm$^2$. The at least one beam of radiation has a plurality of pulses with a pulse duration, $T_p$, less than a thermal diffusion time, $T_d$, of the target neural tissue.

Results demonstrate that efficient optical stimulation wavelengths mirror the tissue absorption spectrum, thus all wavelengths in the IR are capable of stimulation, however, optimal wavelengths do exist that are based on the depth of absorbed pulsed light in tissue. This suggests that the intrinsic tissue absorption properties are primarily responsible for efficient stimulation with minimal tissue damage.

The mechanism of action for this phenomenon is related to establishing a thermal gradient in the tissue (at the level of the neuronal cell membrane) that causes subsequent stimulation due to the increase in temperature. Furthermore, theoretically with the addition of exogenous chromophores in the target tissue, the absorption can be changed based on the material properties of that deposited enhancer. These properties may be optimized to not only absorb light efficiently (thus establish the thermal gradient in tissue) at the appropriate energy levels, but also act as a heat sync to minimize thermal damage in tissue associated with this nerve stimulation phenomenon. With this known thermal mechanism for stimulation of neural tissue, any wavelength of light can be used for stimulation, provided the light is absorbed by the optical enhancing medium and transferred to heat locally near the cell membrane. An optimal wavelength for use of an exogenous chromophore would be one that has minimal absorption in neural tissue, yet optimal absorption (i.e. absorption that is higher than that of the tissue) in the enhancing material. The optimal wavelength for stimulation with an endogenous chromophore would be one that localizes the thermal gradient near the cell membrane without significant absorption from other tissue layers. This known mechanism of action will certainly improve the method of optical stimulation in neural tissue by maximizing efficiency of the phenomenon while at the same time minimizing damage to the tissue.

Theoretically, with the addition of exogenous chromophores in the target tissue, the absorption can be changed based on the material properties of that deposited enhancer. These properties may be optimized to not only absorb light efficiently at the appropriate energy levels, but also act as a heat sink to minimize thermal damage in tissue associated with this nerve stimulation phenomenon. Furthermore, any wavelength of light can be used for stimulation, provided the light is absorbed by the optical enhancing medium. An optimal wavelength for this phenomenon would be one that has minimal absorption in neural tissue, yet optimal absorption (i.e. absorption that is higher than that of the tissue) in the enhancing material. This certainly improves the method of optical stimulation in neural tissue by maximizing efficiency of the phenomenon while at the same time minimizing damage to the tissue.

In one embodiment, experiments using a pulsed alexandrite laser (750 nm) were performed to validate this novel idea on the rat sciatic nerve in vivo. The alexandrite laser operates at a wavelength that has minimal absorption in soft tissue, including neural tissue. Optical stimulation does not occur with low levels of energy incident on neural tissue using this laser. However, by increasing the energy to over 200 times that required for optical stimulation using the optimal wavelength at 2.12 microns, the tissue began to dehydrate and carbonize. With this change in tissue properties, the tissue absorption coefficient increases significantly. Upon inflicting this change in the tissue properties, stimulation threshold over this area therein was significantly reduced. This was the first experiment to demonstrate that a change in absorption properties in nerve tissue may facilitate optical stimulation with a minimally absorbed laser beam.

The biophysical mechanism of the optical stimulation of the neural tissue was further analyzed by careful examination of possible photobiological effects following absorption driven light-tissue interaction. Specifically, a sciatic nerve was stimulated in vivo with the Holmium:YAG laser (2.12 µm), Free Electron Laser (2.1 µm), Alexandrite laser (690 nm), and the commercial prototype solid state laser nerve stimulator built by Aculight (1.87 µm), respectively. Through a process of elimination approach, relative contributions to the optical stimulation were determined from interaction types resulting in the optical stimulation, including temperature, pressure, electric field, and photochemistry. It is demonstrated that neural activation with pulsed laser-light occurs by a transient thermally induced mechanism. Data collected reveal that the spatial and temporal nature of this temperature rise, including a measured surface temperature change required for stimulation of the peripheral nerve (7-10° C.). This interaction is a photo-thermal effect from transient tissue temperature changes, a temperature gradient at the axon level (4.5-6.4° C.), resulting in direct or indirect activation of transmembrane ion channels causing action potential propagation. Stimulation requires that the increase in temperature occur before significant thermal diffusion can occur. Therefore, the laser pulse duration must be significantly less that the thermal diffusion time in the specific neural tissue type (a tissue property). In the case of the peripheral nerve, this is roughly 5-10 msec. It is shown that an exogenous chromophore introduced to a nerve tissue can be used to directly facilitate the stimulation in a wavelength otherwise not absorbed by the nerve tissue, by leading to nerve activation and action potential propagation. Preferably, the chromophores (exogenous or endogenous) is one that maximizes temperature increases while minimizing tissue damage in the target neural tissue.

The method according to the present invention has advantages over the existing optical neural stimulation methodology by: 1) increasing spatial resolution to only the area where exogenous chromophore is loaded or placed, 2) increasing the number of lasers and wavelengths available for optical stimulation by changing the absorption properties of the target tissue (thus allowing stimulation), 3) enhancing existing optimal wavelengths to decrease the amount of laser energy required for stimulation as well as possibly increasing the energy required for tissue damage by acting as a heat sync in the nerve, 4) allowing the possibility of non-invasive stimulation by coating/loading the target neurons prior to stimulation and the use of a laser with a wavelength that is both capable of penetrating soft tissue as well as being highly absorbed by the input chromophore.

Referring to FIG. 1, a system 100 for optically stimulating a neural tissue (sciatic nerve) is shown according to one embodiment of the present invention. The system 100 has an energy source 110 for generating optical energy. The energy source 110 in this embodiment includes a Holmium:YAG laser. The energy source 110 can also be a free electron laser, an Alexandrite laser, a solid state laser, a $CO_2$ laser, a tunable OPO laser system, an $N_2$ laser, an excimer laser, or an Er:YAG laser, or the like.

The optical energy in the embodiment is generated in the form of a beam of pulsed IR light 120 along a first optical path 121. The beam of pulsed IR light 120 has pulses with a pulse duration $T_p$ that is less than a thermal diffusion time, $T_d$ of the sciatic nerve 190.

In operation the optical energy is delivered to a sciatic nerve 190 by a delivering means that optically coupled to the optical source 110. The delivering means is configured to deliver the optical energy with a radiant exposure that causes a thermal gradient in the sciatic nerve 190, so as to stimulate the sciatic nerve 190. In this embodiment, the delivering means includes a mirror 130, a focusing lens 140, a coupler 150, an optical fiber 160 coupled to the coupler 150 and a probe 170 coupled to the optical fiber 160. The mirror 130 is placed between the energy source 110 and the focusing lens 140 along the optical path 121 of the beam of pulsed IR light 120 for transmitting a portion 123 of the beam of pulsed IR light 120 to the focusing lens 140 along the first optical path 121 and reflecting the remaining portion 124 of the pulsed IR light 120 to an energy detector 183 along a second optical path 122 that is perpendicular to the first optical path 121. The portion 123 of the beam of pulsed IR light 120 transmitted to the focusing lens 140 is focused onto the coupler 150 and is then delivered through the optical fiber 160 and the probe 170 to the sciatic nerve 190 for optical stimulation thereof. The optical energy delivered to the sciatic nerve 190 can be determined by measuring the optical energy of the remaining portion 124 of the pulsed IR light 120 by the energy detector 183.

Additionally, the delivering means may also include a movable stage (not shown) that is operably coupled to the probe 170 such that the probe 170 is movable with the movable stage three-dimensionally to selectively deliver the optical energy to one or more neural fibers of the sciatic nerve 190.

As shown in FIG. 1, the system 100 also includes an IR mirror 181 and an IR FPA camera 182 positioned in relation to the sciatic nerve 190 for monitoring the temperature profile (i.e., the thermal gradient) of the sciatic nerve 190 caused by the optical energy delivered from the probe 170. The monitored temperature profile of the sciatic nerve 190 is transmitted to a computer 184 for evaluation and/or display of the optical stimulation of the sciatic nerve 190. In addition, the system 110 also has a trigger 185 coupled between the energy source 110 and the computer 184 for activating and/or controlling the output (intensity and/or wavelength) of the Holmium:YAG laser 110 based on the evaluation of the optical stimulation monitored by the IR FPA camera 182.

These and other aspects of the present invention are more specifically described below.

IMPLEMENTATIONS AND EXAMPLES OF THE INVENTION

Without intent to limit the scope of the invention, exemplary methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Several exemplary experiments were conducted at the Vanderbilt University W. M. Keck Free Electron Laser Center and the Vanderbilt Biomedical Optics Laboratory in accordance with animal protocols approved by the Institutional Animal Care and Use Committee (IACUC).

Example

Biophysical Mechanism Responsible for Low-Level, Transient Optical Stimulation of Peripheral Nerve In vivo neural activation with low-levels of pulsed infrared light [1] exhibits advantages over standard electrical means by providing a contact-free, spatially selective, artifact-free stimulation method [2] that encourages development towards clinical application. In this example, the biophysical mechanism underlying this phenomenon was determined by careful examination of possible photobiological effects following absorption driven light-tissue interaction. Sciatic nerve preparation was stimulated in vivo with the Holmium:YAG laser (2.12 µm), Free Electron Laser (2.1 µm), Alexandrite laser (690 nm), and the commercial prototype solid state laser nerve stimulator built by Aculight (1.87 µm), respectively. Through a process of elimination approach, relative contributions to the neural activation were systematically determined from interaction types resulting in optical stimulation, including temperature, pressure, electric field, and photochemistry. Collectively, the results imply neural activation with pulsed laser-light occurs by a transient thermally induced mechanism. Data collected reveal that the spatial and temporal nature of this temperature rise, including a measured surface temperature change required for stimulation of the peripheral nerve (7-10° C.). This interaction is a photothermal effect from transient tissue temperature changes, a temperature gradient at the axon level (4.5-6.4° C.), resulting in direct or indirect activation of transmembrane ion channels causing action potential propagation.

Methods

All experiments were conducted at the Vanderbilt University W. M. Keck Free Electron Laser Center and Vanderbilt Biomedical Optics Laboratory in accordance with standards set by the Institutional Animal Care and Use Committee.

A. Animal Preparation (Rat and Frog):

Spraque-Dawley rats (300 to 400 g) were implemented for these experiments. In preparation for surgery, 60 rats and 4 frogs were anesthetized with IP injection of ketamine (80 mg/kg) and xylazine (10 mg/kg) solution and maintained under sedative with additional boluses of ketamine for the duration of individual experiments. Once anesthetized, animals were placed in the prone position and the right and left sciatic nerve exposed over the length of the femur. An incision was made posterior-laterally extending from the gluteus muscles to the popliteal region. This allowed access to the sciatic nerve from its exit from the pelvic cavity to the level of the knee and allows for visualization of specific motor branches (n. fibularis and n. tibialis) to the biceps femoris, gastrocnemius, and distal muscles. The muscle fascia overlying the nerve was carefully removed to expose the nerve surface with its epineurial (outer) covering maintained intact. Nerves were continually moistened with normal saline to avoid desiccation during the acute study.

B. Experimental Design and Electrophysiological Evaluation:

Each nerve tested was set up such that optical stimulation could be performed at a point adequately proximal to recording electrodes in the main trunk of the sciatic nerve. Furthermore, a motor branch of the sciatic nerve leading to the biceps femoris muscle was easily identified and allowed observation upon stimulation of motor fibers in the sciatic nerve. Recordings of compound nerve action potentials (CNAPs) were made by placing a bipolar electrode under the nerve at one or two points distal to the point of stimulation. Compound muscle action potential (CMAP) recordings were made by placing needle electrodes (Grass E-2 electrodes; Grass Telefactor, Inc.; West Warwick, R.I.) into the muscle belly in a bipolar fashion (belly-to-belly placement). Responses were recorded with a modular data acquisition system (MP100, Biopac Systems Inc. Santa Barbara, Calif.) controlled using a laptop computer and Acknowledge) software (Biopac Systems Inc.). For the purposes of this study, stimulation threshold was defined as the minimum radiant exposure incident on the peripheral nerve surface required for one visible muscle twitch per laser pulse. Recorded responses served to confirm the evoked stimulation and nerve potential propagation.

C. Laser Setup (Holmium, Alexandrite, Aculight):

Tissue morphology and optical properties determine the distribution and depth of penetration of light energy and the potential for both excitation and damage to the laser irradiated nerve. The literature provides evidence that laser light at 2.1 µm wavelength is optimal for stimulation in the rat peripheral nerve [2]. A portable Holmium:YAG laser (Ho:YAG Model 1-2-3 laser, Schwartz Electro Optics, Inc.) was used in many of these studies. This laser operates at a wavelength of 2.12 µm with pulse duration of 350 µs (Full Width Half Maximum—FWHM). The Ho:YAG laser beam is coupled directly to a 600 µm optical fiber (3M Optical Fiber Power Core, FT-600-DMT), which was mounted on a three dimensional micromanipulator and precisely positioned over the nerve at the identical site of electrical stimulation. The intensity of radiant exposure (0.3-1.0 J/cm$^2$) was controlled via attenuating optical filters. Reported radiant exposures were calculated based on the spot size at the tissue; given the optical fiber diameter, the distance from fiber to tissue, and the numerical aperture of the fiber. Alternately, a Free Electron Laser (2-10 µm) located at Vanderbilt University was tuned to 2.1 µm for pulse duration studies, as well as the first generation of a solid state diode laser device for optical nerve stimulator made by Aculight (Bothel, Wash.) operating at 1.87 µm. Finally, an Alexandrite laser crystal was used for an additional study to examine the effect of a laser induced electric field on nerve stimulation by changing the crystal within the Schwartz Electro Optics 1-2-3 laser to output a wavelength of 750 nm while all other laser parameters remained unchanged.

D. OCT Measurements:

Surface displacement attributable to pressure transients accompanying thermoelastic expansion upon laser irradiation were measured using a differential phase optical coherence tomography (DP-OCT) system from UT Austin [19-21]. This system was employed to make use of its extremely high spatial and temporal resolution measurement capabilities. Rat sciatic nerve tissue was placed in a petri dish hydrated with saline and covered with a thin microscope slide coverslip for ex vivo experiments. The Ho:YAG laser coupled to a 600 µm fiber located 0.75 mm from the tissue was used to irradiate the tissue over a range of radiant exposures (0.3 to 1.0 J/cm$^2$). Differences in fringe signals from the surface of the nerve tissue relative to the overlying coverslip (reference position) allowed real time measurement of the surface displacement following each laser pulse with a spatial resolution of 20 nm sampled at 1 MHz. An optical trigger facilitated synchronous recording of the exact timing of pulse delivery for all experiments.

E. Piezoelectric Experiments:

The prospect of pulsed stress waves leading to a stimulatory effect in neural tissue was investigated in vivo with a custom made mechanical piezoelectric element. A piezo actuator (NA-09 Piezo Actuator, DSM, Franklin, Tenn.) with a 9 micron range rated for a total voltage range of −30/+120 V was designed and assembled into a structure (3×1×1 cm) with a mounting base and location for an output tip. The removable threaded tip insert consisted of a 1 mm diameter fabricated ceramic sphere oriented in the direction of motion of the actuator. This tip design mimicked the shape and size of a Gaussian shaped Ho:YAG laser beam from a 600 micron fiber located 0.75 mm from the target tissue just at the surface of the irradiated nerve. The actuator's open loop displacement versus applied voltage was characterized to produce a constant velocity move based on DP-OCT data collected regarding surface displacement using threshold radiant exposures with the Ho:YAG laser (at least 300 nm in 350 microseconds). The actuator was connected to a linear amplifier (VF-2000, DSM, Franklin, Tenn.) with an input voltage gain of 21.3. The entire system was computer controlled by a software program (Labview, National Instruments, Austin, Tex.). Triangle and sinusoidal input waves corresponding to an increase and decrease in actuator position allowed for fast pressure transients to be delivered to the surface of the sciatic nerve in vivo. CNAP and CMAP recordings were triggered from the onset of actuator motion to observe any stimulatory effect from expansion and compression waves. The range of displacement amplitudes used paralleled measurements of thermoelastic expansion and the time for the total displacement was held at 350 µsec, the length of the Ho:YAG laser pulse.

F. Cold Frog Experiments:

Experiments in frog sciatic nerve examined the temperature dependence of stimulation threshold. The frog was chosen as the best model for these experiments due to its cold blooded nature, and ability to maintain nerve conduction over a wide temperature range. To determine temperature values of the bath, a wire thermocouple (Type E, Chromel/Constantin, Omega Engineering Inc., Stamford, Conn.) was suspended in the fluid and temperature values were recorded at a rate of 500 Hz using a data acquisition system (Labview, National Instruments, Austin, Tex.) The nerve and optical fiber were submerged in saline maintained at temperatures of 0 and 25° C. Time between trials (10 minutes) allowed for adequate heat diffusion to tissue and thus this study assumes the temperature of the bath and the tissue is identical. This also helped minimize tissue dehydration, which can drastically affect the stimulation threshold. A 600 µm fiber coupled to the Ho:YAG laser was placed 0.4 mm from the nerve surface and stimulation thresholds recorded for 3 trials at each temperature for each nerve (n=6).

G. Two Dimensional Radiometry of Irradiate Tissue Surface:

Two dimensional radiometry was used to observe the irradiated tissue surface temperature profile in both time and space. FIG. 1 illustrates the Indigo Systems infrared (thermal) camera with Phoenix data acquisition system, located in UT Austin [22], used for gathering temperature profiles in vivo upon Holmium:YAG laser stimulation of the rat sciatic nerve at 2 Hz. A 600 µm fiber was coupled to the laser and held at a constant distance of 0.5 mm from the tissue during all trials. Recordings were taken for 1 second at a sampling rate of 800 kHz. Temperature data was normalized and output as a function of time and position (x, y). Measurements of the surface temperature of the nerve in the two dimensional plane (10 cm×2.5 cm FOV) were observed both during and after the laser pulse. Measurements using a range of radiant exposures from stimulation threshold to radiant exposures causing thermal changes in tissue (0.3-0.9 J/cm$^2$) were conducted in hydrated nerve tissue (n=18).

Results

A. Electric Field:

Maxwell's EM theory suggests an inherent electric field exists within laser light, which is associated with the propagation of light itself and driven by time and space varying electric and magnetic fields [23]. Since the conventional method uses electricity to excite axons, questions arise whether the electric field within the incident light beam is large enough to directly initiate action potentials. Consider the following equation:

$$S_{threshold} = \tfrac{1}{2} c \epsilon_0 E_{max}^2, \qquad (1)$$

where threshold laser radiant exposure ($S_{threshold}$)=0.32 J/cm$^2$ with the Ho:YAG laser, the speed of light (c)=3e$^{10}$ cm/sec, permittivity of neural tissue ($\epsilon_0$) (c$\epsilon_0$=0.002634 A-s/V-m)[24]. The calculated theoretical value for the maximum instantaneous intensity of the electric field ($E_{max}$) at the tissue surface is 0.155 V/mm$^2$.

The Alexandrite laser operating at 750 nm (red light) was used to attempt stimulation of the peripheral nerve. The Ho:YAG laser crystal and mirrors typically used for optical stimulation experiments were replaced with the Alexandrite crystal and mirrors. In this setup laser parameters and beam characteristics remained constant (i.e. pulse duration, fiber size, spot size, repetition rate, and electric field strength) except wavelength, which changed from a fairly high absorption (Ho:YAG, $\mu_a$=333 µm) to a very low absorption (Alexandrite, $\mu_a$=106 µm) in soft biological tissue. A total of 4 nerves were irradiated through a range of radiant exposures from stimulation threshold to those causing thermal changes in the tissue (0.3 J/cm$^2$ to 51.7 J/cm$^2$). The Alexandrite laser did not stimulate the peripheral nerve in any trial using radiant exposures up to 150 times Ho:YAG stimulation threshold. As a side note, these results provide experimental evidence that the laser electric field does not stimulate neural tissue. However, upon tissue dehydration and carbonization using radiant exposures greater than 50 J/cm$^2$ the laser was able to repeatedly stimulate the nerve.

Figure 2:
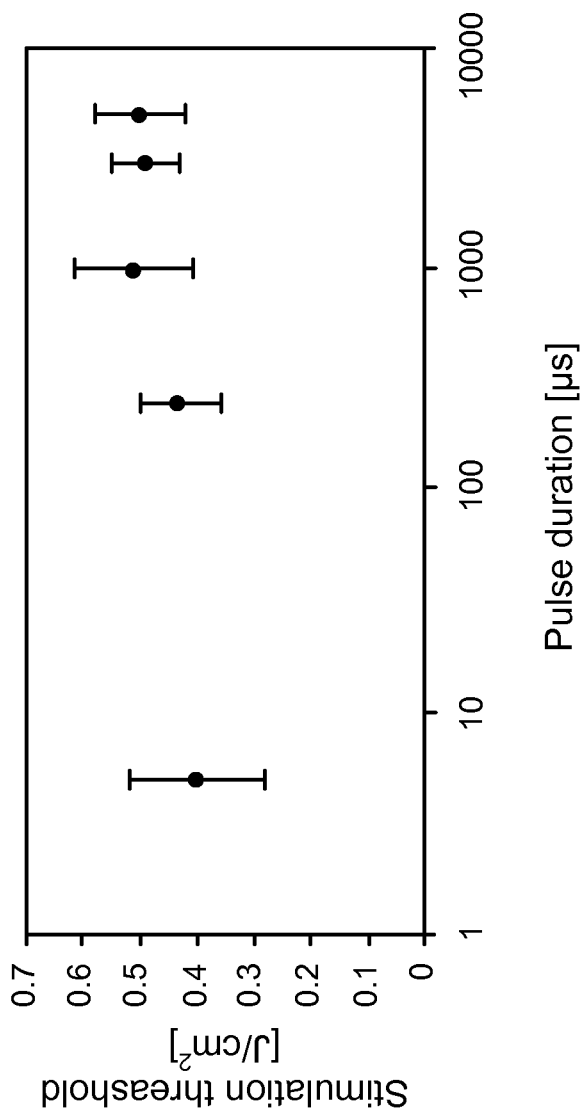
FIG. 2 shows an effect of laser pulse duration on stimulation threshold radiant exposure. Three lasers with comparable tissue absorption coefficients were used; the FEL (5 μsec), Ho:YAG (350 μsec), and tunable solid state Aculight laser (1-5 msec). All lie well outside stress confinement, but are still thermally confined.

B. Photomechanical:

This study examined plausible photomechanical effects leading to optical stimulation; namely thermoelastic expansion or pressure wave generation from rapid heating. Contributions from pressure waves to optically stimulate the peripheral nerve were studied by observing the effect of varying pulse duration on stimulation threshold. FIG. 2 depicts the effect of varying pulse width on the minimum incident radiant exposure required for an action potential using three lasers with nearly equivalent absorption coefficients, or depths of penetration ranging from 333 to 450 µm; the FEL (2.1 µm, 5 µs), Ho:YAG (2.12 µm, 350 µs), and tunable solid state Aculight laser (1.87 µm, 1-5 msec). Hence, stimulation threshold was established for 5 different pulse durations (5 µsec, 350 µsec, 1 msec, 3 msec, 5 msec) for 10 trials each. It is clear from this figure that the threshold radiant exposure required for stimulation at this tissue absorption does not significantly change with variable pulse width through almost 3 orders of magnitude, including those pulse durations that lie well outside of the stress confinement zone. These data along with an understanding of photomechanical interactions directly contradict the notion that pressure waves generated from rapid heating are responsible for optical nerve stimulation. This idea is discussed in detail within the discussion section.

The next set of experiments focused on mechanical stimulation from thermoelastic expansion in tissue upon tissue absorption and subsequent heating by internal conversion. It is very difficult, if not impossible, to design in vivo optical stimulation experiments that decouple temperature rise and associated pressure transients. In a set of shrewdly designed experiments the thermoelastic expansion of the nerve surface was measured over the typical range of radiant exposures required for peripheral nerve excitation. Results helped characterize the amplitude of mechanical pressure waves, which were injected into the tissue in a second series of experiments. Thus, the thermal and mechanical effects were disassociated so that the mechanical effects within the nerve from thermoelastic expansion could be observed independently.

Figure 3:
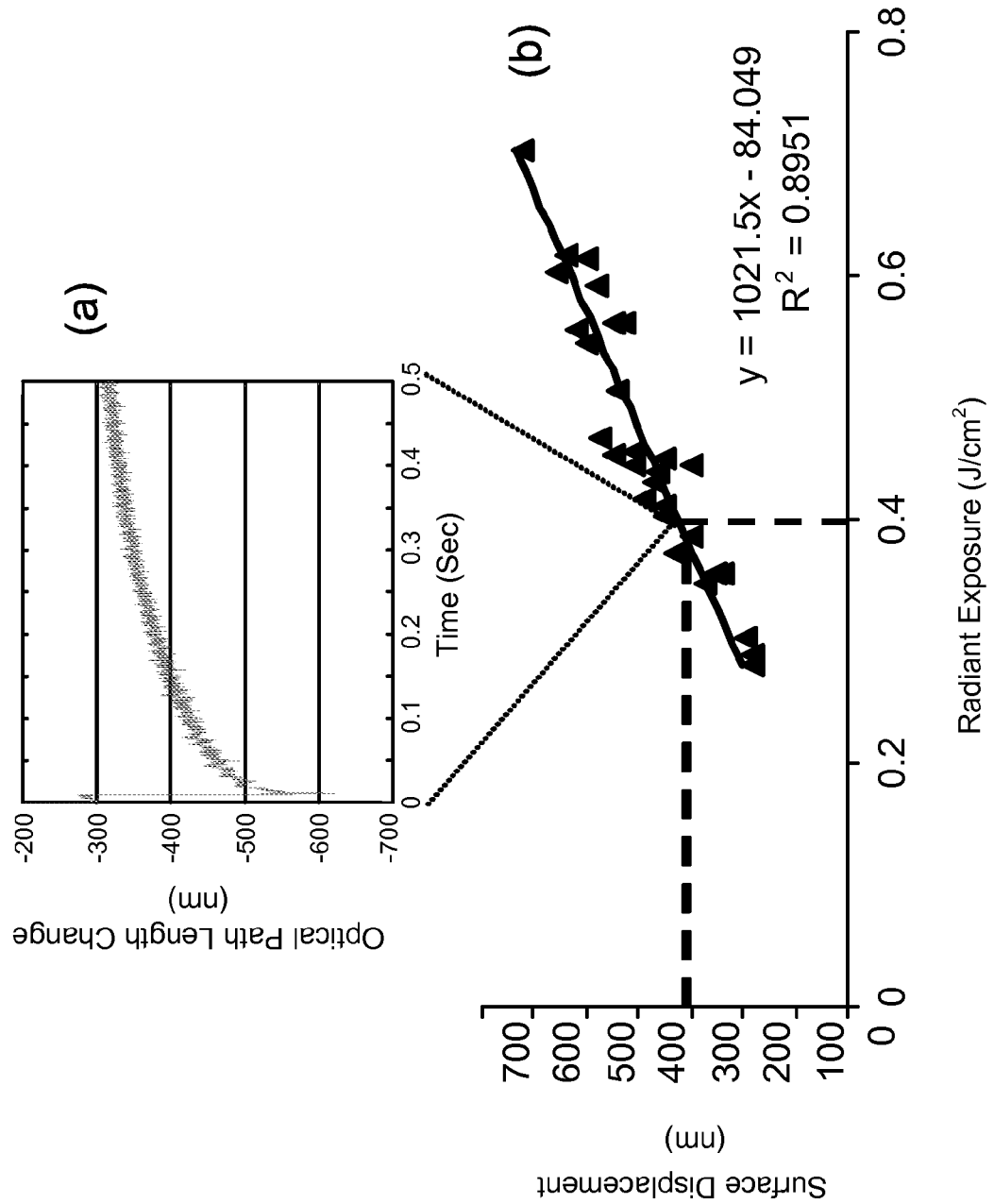
FIG. 3 shows DP-OCT measurements of nerve surface displacement resulting from Ho:YAG laser irradiation, (a) a typical recording of the optical path length change of the nerve surface relative to a stationary coverslip from near threshold radiant exposure (0.4 J/cm2) indicating thermoelastic expansion on the order of 300 nm, and (b) a total of 18 measured surface displacements over the normal range of use for optical stimulation radiant exposures.

Tissue displacement during the laser pulse was measured using a phase sensitive OCT setup from UT Austin [20] to test the actual magnitude of tissue thermoelastic expansion from optical stimulation. The typical nerve displacement in time measured from this system during a single laser pulse is seen in FIG. 3a. Notice the rapid increase in optical path length change and exponential decay of the waveform. This maximum value corresponds to immediate absorption, heating and maximum thermoelastic expansion resulting from the laser pulse. Note in the example that the time required for the maximum displacement to occur is 350 µsec, the pulse width of the Ho:YAG laser. The exponential decay in displacement represents the typical thermal decay in tissue based on the thermal diffusion time, a tissue property. FIG. 3b describes the maximum change in surface displacement of 3 rat sciatic nerves (ex vivo) upon irradiation with Ho:YAG laser over the typical physiologic range of radiant exposures for optical stimulation. As expected, displacement increases linearly with laser radiant exposure, theoretically supported by the following equation:

$$\Delta P = (1/\gamma)(\Delta V/V)^* \Delta T, \quad (2)$$

where the change in pressure ($\Delta P$) is linearly proportional to the change in temperature ($\Delta T$) and related by the product of the inverse of the coefficient of isothermal compressibility ($\gamma$ in units [Pa$^{-1}$]) and the ratio of the change in volume ($\Delta V$) over the total irradiated volume (V). Surface displacement slightly above threshold (0.4 J/cm$^2$) was measured to be 300 nm. Hill et al reported membrane displacement measurements of 1.8 nm from the normal physiologic rapid change in cell diameter in crayfish giant axons following electrical stimulation [25]. Thus while a displacement of 300 nm in a 350 µsec pulse width is very small this value can not be considered negligible since it is much greater than rapid displacements experienced by the typical axon.

Quantitative data on the exact amplitude and duration of the pressure transients secondary to tissue temperature changes from pulsed laser irradiation provided the framework for the design of a piezoelectric actuator that mimics beam characteristics in optical stimulation. Similarly between spot size of the typical laser beam used in DP-OCT experiments and actuator tip helped normalize the effective tissue volume changes upon tissue displacement (see Equation 2). In the example, pressure transients are extricated from temperature increases to examine the effect, if any, from simulated photomechanical stimulation of the peripheral nerve. For these studies a variety of mechanical pulse wave shapes and amplitudes were delivered to a total of 10 rats (20 nerves). For each nerve, both triangle and sinusoidal shaped waveforms varying in amplitude from 300 nm to 9 microns were delivered normal to the surface of the nerve via the beam shaped actuator tip. Based on displacement measurements, the maximum temperature rise occurs 350 µsec after onset of the laser pulse (the pulse width of the Ho:YAG). Compression and expansion waveforms were delivered in this 350 µsec time course for all experiments. Results reveal that pressure transients delivered to the nerve surface in a manner analogous to laser induced thermoelastic expansion waves are not capable of initiating action potentials with amplitudes at least 30 times those measured for optical nerve stimulation threshold.

Figure 4:
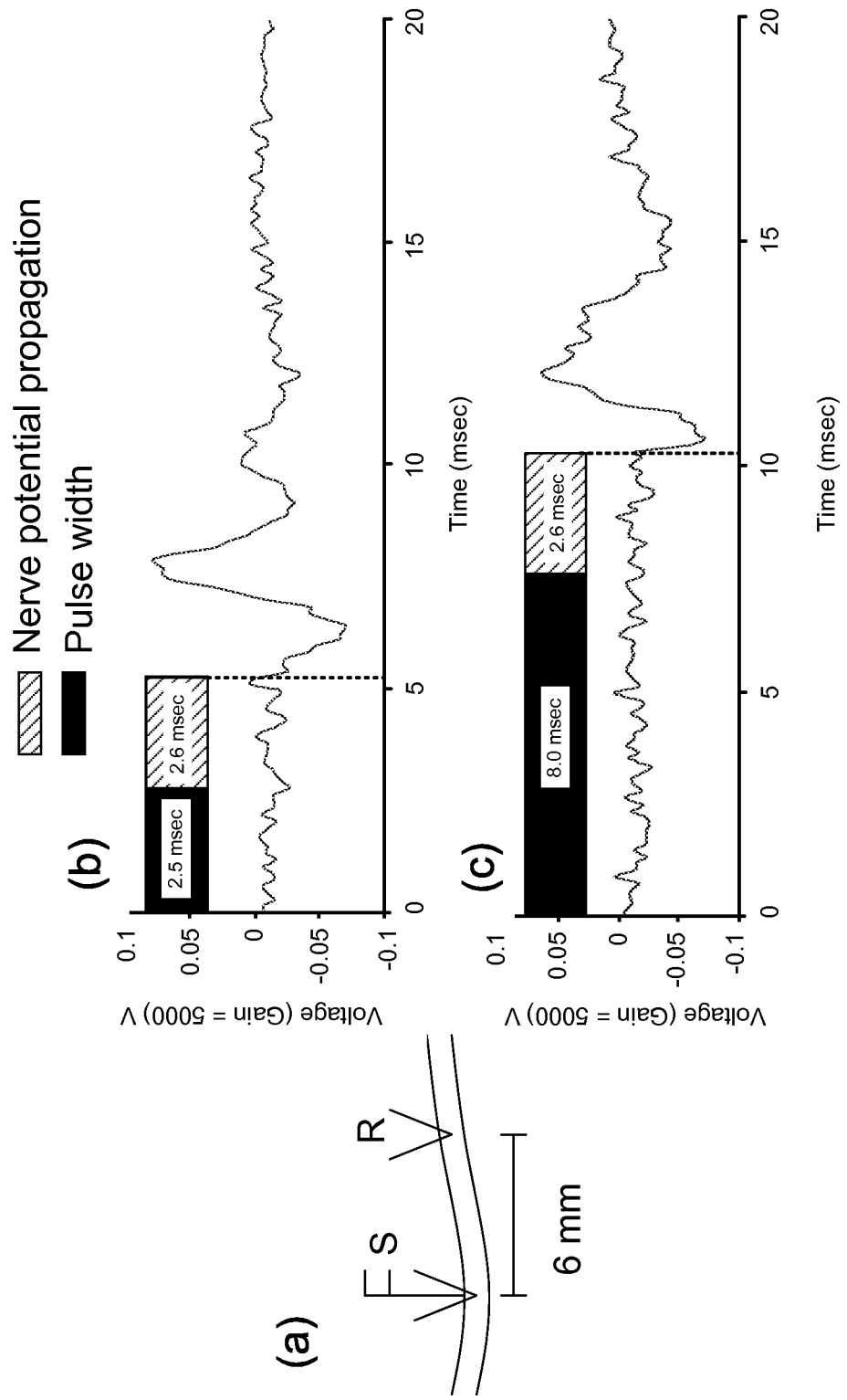
FIG. 4 shows CNAP signal onset time for two different pulse durations. Assume the time for conduction is constant after the pulse energy deposition, (a) Schematic illustrating the distance from stimulation and recording for (b) and (c), (b) CNAP recorded from stimulation at t=0 using a 2.5 msec pulse duration with the Aculight optical nerve stimulator, and (c) CNAP recorded from stimulation at t=0 using a 8.0 msec pulse duration with the Aculight optical nerve stimulator. These recording prove that all laser energy is required before the onset of the CNAP can occur.

C. Photothermal:

To provide compelling evidence for a photothermally mediated mechanism, the effect of pulse width changes on the onset time for stimulation and action potential propagation was observed. CNAP's were recorded exactly 6 mm distal to the site of rat peripheral nerve stimulation upon optical stimulation from Aculight's portable optical nerve stimulator (1.85 µm). The tunable pulse width was employed to observe changes in the onset time for the action potential with variable laser pulse durations. FIG. 4 depicts the recorded CNAP's from identical stimulation and recording sites in one nerve using 2.5 msec and 8.0 msec laser pulse lengths (shaded rectangles), all additional laser parameters were constant for each trial. Laser radiant exposure was held constant and slightly above threshold for each recording (0.4 J/cm$^2$) as indicated by the similar amplitudes of peak CNAP. It is reasonable to assume that the conduction velocities for the recordings in FIGS. 4*a* and 4*b* are identical because similar motor axons were recruited for each trial, yielding a conduction time for both CNAP's of 2.6 msec. The most notable observation from this study is that the onset time for stimulation varies with width of the laser pulse. This implies that all laser energy must be deposited in the tissue before action potential propagation can occur.

Figure 5:
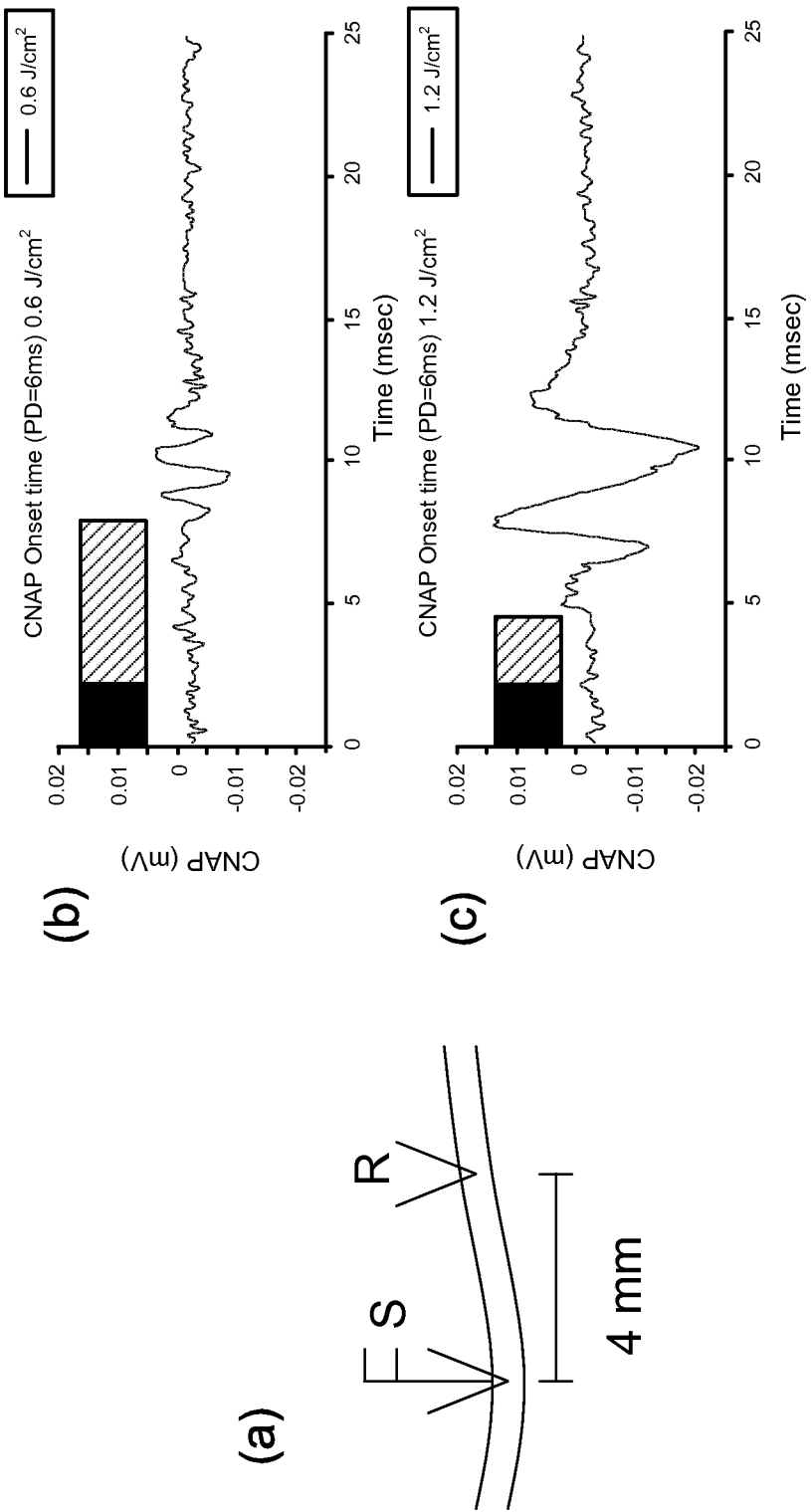
FIG. 5 shows an effect of laser radiant exposure on time of CNAP recording onset stimulated at t=0 using a 6 msec pulse width with the Aculight optical nerve stimulator. (a) schematic illustrating the distance from stimulation and recording for (b) and (c), and (b) CNAP recorded from optical stimulation with 0.6 J/cm², and (c) CNAP recorded from optical stimulation with 1.2 J/cm². These recording illustrate that a specific tissue temperature change is required for the onset of the CNAP can occur.

A study was performed to detect changes in onset time of the CNAP response upon optical stimulation with varying laser radiant exposure to augment understanding of mechanistic contributions based on temperature. FIG. 5 depicts CNAP recordings stimulated (t=0) with a 6 msec pulse width using the tunable pulse Aculight optical nerve stimulator. CNAP's were recorded 4 mm from the stimulation site for each recording, shown in FIG. 5*a*. All experimental variables and laser parameters were held constant during stimulation and recording of FIGS. 5*b* and 5*c*, with the exception of the laser radiant exposure, 0.6 J/cm2 and 1.2 J/cm2, respectively. The onset time of the response in FIG. 5*b* is 7.8 msec following the laser pulse and 4.8 msec for FIG. 5*c*. Again a constant conduction time for both recordings was assumed (1.8 msec). It is clear from these traces that as the optical energy used for stimulation is increased, the onset time for the CNAP occurs in a shorter time.

The effect of nerve tissue temperature on the threshold radiant exposure required for stimulation was determined. The cold blooded amphibian nerve temperature was manipulated in a saline bath in vivo to facilitate nerve stimulation at temperatures of 0 and 25° C. Time between trials (10 minutes) allowed for adequate heat diffusion from bath to tissue and thus this study assumes the temperature of the bath and the tissue is identical. Both the optical fiber for stimulation and the peripheral nerve were submerged in the temperature controlled saline solution and held at a distance 0.4 mm away. This caused the reported threshold radiant exposures for stimulation to increase as the saline between the fiber and tissue absorbed much of the optical energy. Since this is a comparative study all experimental parameters remained unchanged for each trial to normalize collected threshold data. Stimulation threshold averages at 25° C. were 0.91 and 0.84 J/cm$^2$ for the two frogs studied with 3 trials for each nerve (n=6). Similarly, average thresholds for stimulation at 0° C. were 1.01 and 0.86 J/cm$^2$, (n=6) respectively. These results indicate no significant change in threshold occurs with changes in nerve tissue temperature.

Photothermal effects result from the transformation of absorbed light energy to heat, which may lead to coagulation or ablation of the target tissue depending on tissue optical properties and laser radiant exposure. Two-dimensional radiometry of the irradiated tissue surface was performed to gain a better understanding of the thermal processes and actual tissue temperature values required for optical nerve stimulation. Using this technique, the temperature profile in space and time were observed following Ho:YAG laser stimulation. FIG. 4 contains the surface temperature profile (x, y) of the single frame containing the maximum temperature value recorded for all frames (800 frames in 1 sec recording) irradiating the nerve with threshold radiant exposure (0.4 J/cm$^2$). This corresponds to the first frame in which all laser energy has been deposited in the nerve tissue. The two graphs below contain the temperature profile for the column (right) and row (left) containing the maximum temperature pixel. The solid lines represent the best Gaussian fit for each temperature profile in space. Peak tissue temperature for this trial upon optical nerve stimulation in vivo (well hydrated tissue) was measured to be 35.86° C. This is a peak temperature rise of 8.95° C., yielding an average temperature rise across the Gaussian laser spot of 3.66° C. with radiant exposures near stimulation threshold. This is very close to the theoretically calculated average temperature rise for a uniform beam with the same laser parameters and neglecting scattering equal to 2.87° C.

Thermal measurements of the rat sciatic nerve surface (n=18) were taken in vivo for each nerve using a range of radiant exposures from 0.3-0.9 J/cm$^2$ in well hydrated tissue. FIG. 7*a* represents the data collected for the maximum surface temperature for a single trial (diamonds) and peak temperature rise in tissue (squares) immediately following laser stimulation as a function of radiant exposure. FIG. 7*b* describes the average thermal gradient, temperature rise from baseline, as a function of laser radiant exposure for all trials (n=18). Clearly, nerve temperature increases linearly with laser radiant exposure. Results predict the minimum temperature increase of the nerve surface required for stimulation (0.3-0.4 J/cm$^2$) is as low as 6° C., yielding a peak temperature of 31° C., provided that the laser pulse width is sufficiently short (<10 msec). Minimum temperatures for onset of thermally induced changes in mitochondria function and protein denaturation are shown in FIG. 7*a*. In the case of non-hydrated tissue (data not shown), the temperature as a function of radiant exposure shifts upward due to a difference in optical properties compared with higher water content tissue. In the example, the mitochondrial damage will theoretically begin to occur between 0.5-0.6 J/cm$^2$; thus illustrating the importance of tissue hydration for safer, more efficient nerve excitation.

Figure 8:
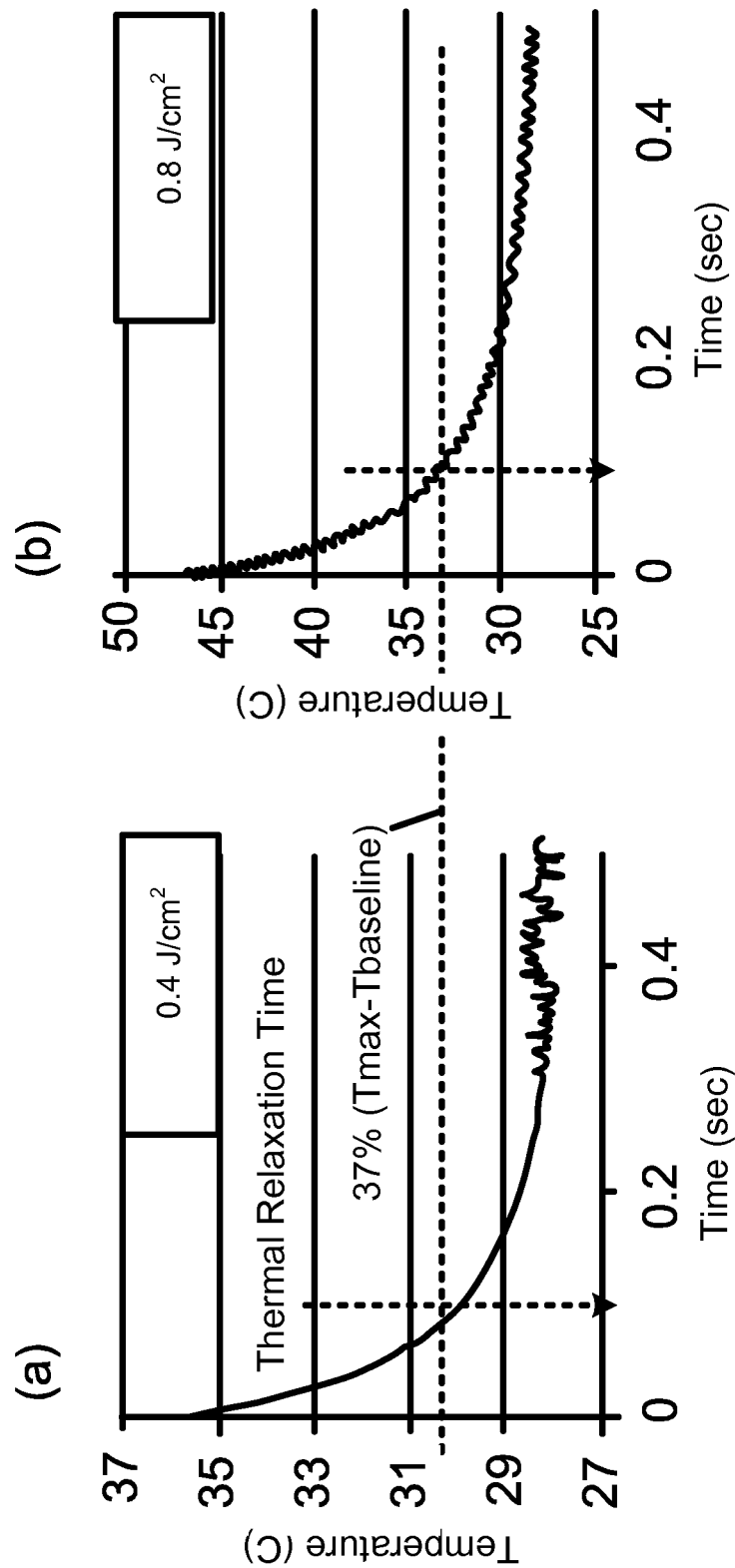
FIG. 8 shows a temperature profile of peripheral nerve in time, laser stimulation near threshold (0.4 J/cm²) (a) and at over 2 times threshold (0.8 J/cm²) (b). The experimental thermal relaxation time of peripheral nerve tissue based on the equation shown in the figure is 90 msec.
Figure 9:
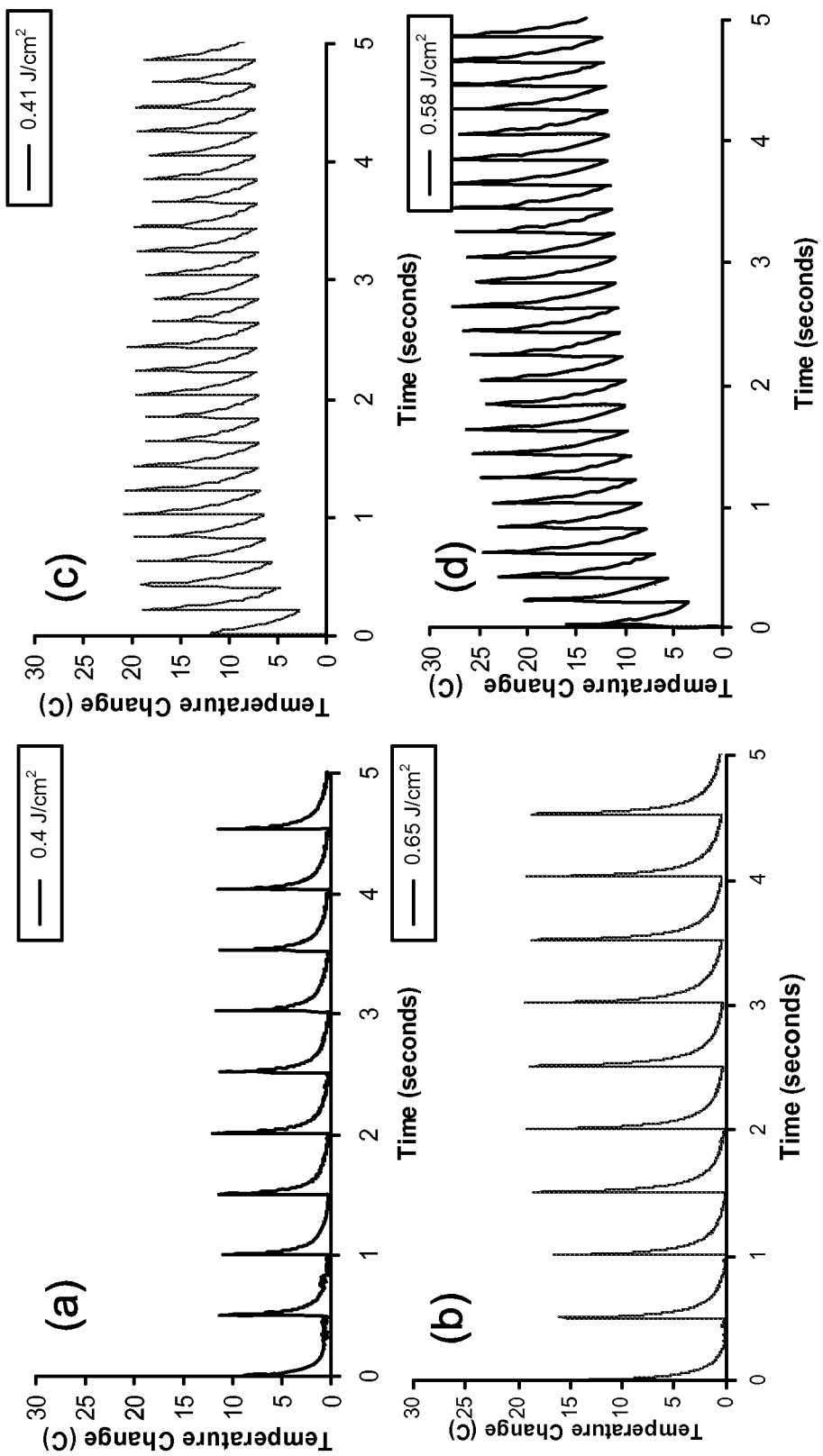
FIG. 9 shows a steady-state maximum temperature increase in nerve tissue from Ho:YAG laser stimulation, (a) temperature rise from 0.45 J/cm² radiant exposure pulses at 2 Hz stimulation frequency, (b) Temperature rise from 0.65 J/cm² radiant exposures at 2 Hz stimulation frequency, (c) temperature rise from 0.41 J/cm² threshold radiant exposures at 5 Hz stimulation frequency, and (d) temperature rise from 0.63 J/cm² threshold radiant exposures at 5 Hz stimulation frequency.

The peripheral nerve temperature profile in time was also observed using the infrared camera. Results from Ho:YAG laser stimulation slightly above threshold (0.4 J/cm$^2$) and at two times threshold radiant exposure (0.8 J/cm$^2$) are shown in FIG. 8. These graphs provide the peak temperature at the height of the Gaussian spatial profile for each frame in time following a single laser pulse at t=0. The exponential decrease of temperature in time represents a typical thermal decay in the nerve tissue. Thermal relaxation time (i.e. the time to dissipate heat absorbed from a laser pulse) is defined as the time for the temperature of the tissue to return to 1/e (37%) of the maximum tissue temperature change. In the case of the rat peripheral nerve, as shown in FIG. 8, the thermal relaxation time was estimated to be about 90 msec. Notice that the thermal relaxation time is independent from laser radiant exposure. Temperature superposition, or additive temperature effects from multiple pulses, was observed for a period of 5 seconds using 2 Hz and 5 Hz stimulation frequencies. These results are shown in FIG. 9. It is clear that the temperature increase and return to baseline tissue temperature is consistent upon multiple laser pulses with a frequency of 2 Hz regardless of laser radiant exposure. This demonstrates that there are no additive temperature effects in peripheral nerve tissue with low frequency stimulation near threshold. A frequency of 5 Hz does have temperature superposition effects as the tissue temperature increase does not return to baseline prior to absorption and heating from the next pulse in the sequence. This quickly leads to a much larger maximum temperature in the tissue than seen with 2 Hz stimulation. The larger radiant exposure will result in more pulses required to reach a maximum temperature steady state as more thermal energy must dissipate to surrounding tissue through heat conduction.

Discussion

A. Process of Elimination Approach for Uncovering the Biophysical Mechanism:

Results presented in this example provide both theoretical and experimental evidence that the electric field inherent in laser light is not responsible for the low level laser excitation of neural tissue. Calculations based on experimental data predict this stimulation mechanism is unlikely. The maximum current delivered to the tissue surface during threshold optical stimulation was 0.05 mA/mm$^2$. This theoretical prediction is between three and four orders of magnitude below the electrical stimulation threshold for peripheral nerves determined in the previous studies, where 0.95+/−0.58 A/cm$^2$ was required for surface stimulation. Moreover, it is important to realize that the electric field owing to light oscillates at $10^{14}$-$10^{15}$ Hz, which was again orders of magnitude higher than the typical electrical stimulation field oscillator frequency. To experimentally test this proposition, the visible alexandrite laser operating at 750 nm was used to attempt optical nerve stimulation. This wavelength, unlike the Ho:YAG wavelength, has minimal absorption in soft tissue, however, the electric field of intensity is similar regardless of wavelength. Thus, any stimulation reported is a direct result of the electric field of the laser light, not from absorption driven photobiological effects. A direct electrical field is highly unlikely as a means for optical stimulation since light from the alexandrite laser did not stimulate at radiant exposures, and therefore a maximum electric field, greater than 100 times higher than those used for the Ho:YAG laser. The results from these experiments do support a thermally mediated mechanism. Heating of the tissue at damaging radiant exposures resulted in stimulation of the tissue. The carbonization and dehydration ('burning') of the nerve significantly changed the optical and thermal properties of the tissue. In this case the tissue absorption for this wavelength increased and immediately mediated the stimulatory effect. This evidence supports an absorption driven process as the biophysical mechanism underlying optical stimulation.

Photochemical effects from laser irradiation depend on the absorption of light to initiate chemical reactions. In the embodiment, it is examined whether the mechanism for transient optical nerve stimulation is a result of photochemical effects from laser tissue interaction. Previous studies have shown that stimulation threshold exhibits a wavelength dependence based on the absorption coefficient of nerve tissue. Optimal wavelengths have a penetration depth of 300-500 microns, however, all infrared wavelengths with sufficient tissue absorption can cause neural stimulation. The stimulation thresholds in the infrared part of the spectrum in essence follow the water absorption curve [1] suggesting that no "magical wavelength" has been identified. This effectively disproves the notion that a single tissue chromophore is responsible for any direct photochemical effects. This also provides some evidence that the effect is directly thermally mediated or a secondary effect to photothermal interactions (i.e. photomechanical effects) as tissue absorption from laser irradiation can be directly related to the heat load experienced by the tissue. Theoretically, one can predict that a photochemical phenomenon is not responsible since infrared photon energy (<0.1 eV) is too low for a direct photochemical effect of laser tissue interactions and insufficient for any multiphoton effects [26, 27].

Figure 10:
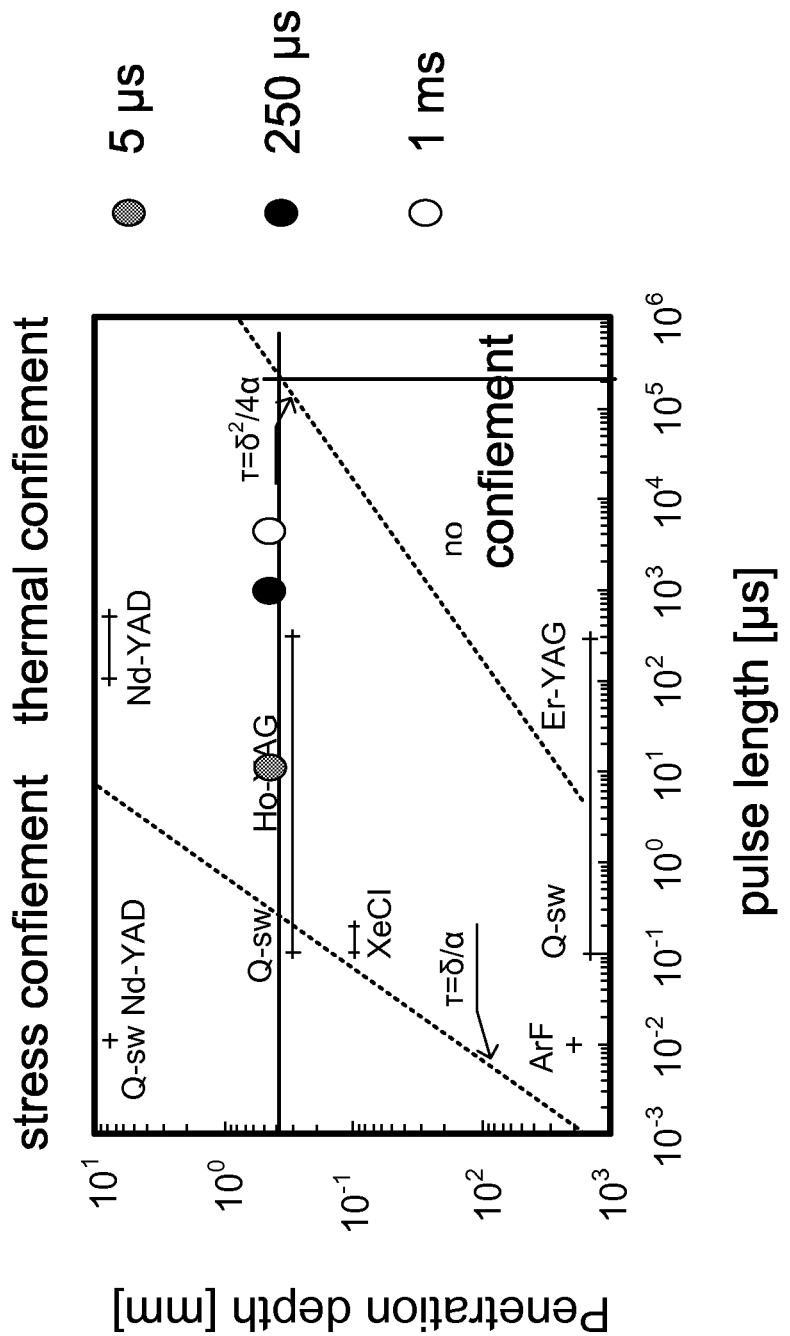
FIG. 10 shows confinement zones based on penetration depth and pulse length for soft tissue. Note that that the three lasers used are all thermally confined, but not stress-confined.

Photomechanical effects produce forces, such as explosive events and laser-induced pressure waves, which can impact cells and tissue. Since it is been operating well below the ablation threshold, ablative recoil can be excluded as a source of mechanical effects. Nerve stimulation using pressure waves (rapid mechanical displacement, ultrasound) is well documented in the literature [28, 29]. The results section described experimental data that discounts the two plausible photomechanical effects leading to optical stimulation; thermoelastic expansion or pressure wave generation from rapid heating. As mentioned previously, relationship between laser penetration depth and pulse duration provide critical information concerning confinement of the laser energy in both space and time. FIG. 10 is a well known graph in tissue optics that depicts the relationship between these two laser parameters to define theoretical zones separating stress confinement, thermal confinement, and no confinement of the laser pulse. The three lasers used in the comparison between pulse duration and stimulation threshold (as shown in FIG. 2) are labeled in FIG. 10. Note that each of these lasers is thermally confined, or the pulse width is adequately short to curtail heat diffusion during the pulsed energy deposition. Similarly, the pulse width is satisfactorily long such that stress effects and pressure wave propagation are minimal. If it is assumed that some level of pressure transients are generated in tissue and these waves result in tissue stimulation, then it would be expected that the stimulation threshold to decrease (i.e. it becomes easier to stimulate using the FEL 5 µsec pulse) the closer a laser lies to the stress confinement zone. However, it is clearly to see the difference in threshold radiant exposures is not significant over three orders of magnitude change in pulse duration with equivalent penetration depths across the thermal confinement zone. Thermo-elastic expansion will always result from heating tissue; however, pressure waves are not generated in tissue with these experimental parameters for optical stimulation.

Given that there is strong evidence against laser-induced pressure waves underlying the optical stimulation mechanism (the pulse duration is too long to facilitate stress confinement and indeed negligible stress transients were measured) and given the fact that no significant difference was found in stimulation thresholds from the three laser sources, despite a 1000 fold difference in pulse duration, it is plausible to assume that stimulation is not dependent on the pulse duration provided the pulse is short enough to minimize heat diffusion during the laser pulse (i.e. conditions of thermal confinement are fulfilled). Although theory predicts that the pulse length may be stretched up to 100's msec before no confinement is achieved (see FIG. 10), experimentally this is an overestimate. Heat diffusion begins immediately (see FIG. 8), which causes the quality of the evoked potentials to be significantly diminished with laser pulse widths greater than 10 msec. Pulses delivered in a time less than this value result in crisp potentials with every pulse, however, pulses longer than 10 msec tend to have a more intermittent and lethargic response. In the case of motor axon stimulation this functionally presents as an irregular and disjointed muscle contraction as opposed to a fast, reliable twitch with shorter laser pulse durations.

While it is possible that pulsed laser irradiation induces pressure waves in the target tissue owing to the thermoelastic effect, the contributions of this to optical stimulation are expected to be minimal with the laser parameters used; pulse duration of 350 µs exceeds the stress confinement time for this wavelength by nearly 3 orders of magnitude resulting in a dissipation of thermally induced expansion during the laser pulse and consequently little pressure buildup [30, 31]. The results from DP-OCT surface displacement measurements support this notion and identify the exact relationship between laser radiant exposure and the subsequent upper limit in magnitude of thermoelastic expansion in nerve tissue. Results from the successive piezoelectric actuator experiments reveal that pressure transients delivered to the nerve surface in a manner analogous to laser induced thermoelastic expansion waves are not capable of initiating action potentials with amplitudes at least 30 times those measured for optical nerve stimulation threshold. These experiments prove that temperature induced volumetric expansion is trivial for radiant exposures much greater than threshold and indicate that the mechanism lacks photomechanical contributions.

B. Supporting Evidence for a Photothermal Mechanism:

Through this process of elimination approach to divulge the mechanism responsible for transient optical stimulation of nerves, it is systematically shown that electric field, photochemical and photomechanical effects from laser tissue interactions do not result in excitation of neural tissue. Thus, the laser stimulation of nerves is mediated by some photothermal process resulting from transient irradiation of peripheral nerves using infrared light. The spatial and temporal thermal transients following optical stimulation of peripheral nerve for the physiologically valid range of radiant exposures implemented with this methodology.

Despite the fact that the process of elimination approach suggests the mechanism is purely a thermal effect in the tissue driving action potential stimulation, proof of this concept has fundamental significance. Results shown in FIG. 4 clearly show that all optical energy must be absorbed by the incident peripheral nerve before any stimulatory effect can occur. This implies that, in the absence of pressure transients, the tissue must sustain some minimal thermal change before excitation of the underlying axons can occur. In subsequent paragraphs the nature and magnitude of the mandatory temperature change will become apparent. These results further illustrate the importance of pulse width in optical stimulation; predicting that longer pulses will increase the time required for an evoked CNAP and decrease the probability of stimulation due to onset of thermal diffusion in tissue. Further proof of the thermal nature of the biophysical mechanism lies in results from the Alexandrite laser stimulation of the peripheral nerve. As optical and thermal properties in the tissue changed from tissue dehydration, the absorption of the alexandrite increased and subsequently a decrease in the stimulation threshold radiant exposures was reported. Again, these results clearly support a thermally mediated excitation means.

A mechanism that is thermally sustained naturally introduces query as to the nature of the temperature change required in the tissue, which is determined by questioning whether this stimulatory thermal change requires a minimum absolute value or rather a thermal gradient, a time dependent temperature change. Results discussed to this point validate either claim, however, data collected regarding temperature dependence on stimulation threshold help to make this distinction. Results from the threshold dependence on nerve tissue temperature experiments demonstrate no significant change in the radiant exposure required for stimulation with changes in tissue temperature. This is despite the fact that a tissue temperature change of 25° C. in the nerve air interface experimental setup requires a radiant exposure of at least 1 J/cm$^2$ (see FIG. 7). The radiant exposures necessary for this temperature change in the saline submerged nerve interface experimental setup (i.e. frog temperature experiments) will require a much larger radiant exposure for a 25° C. change, at least two times the energy used for stimulation. Regardless, the stimulation thresholds are not significantly different across a large tissue temperature range, varying by an average of 6% between trials. From these results, it is concluded that there is no set threshold tissue temperature that must be reached to initiate the action potential, as the threshold for optical stimulation does not change with large tissue temperature differences upon laser pulses associated only with small increase in tissue temperature. Thus, the mechanism for optical stimulation is temperature dependant and a transient phenomenon requiring a certain increase in temperature in a given short time (i.e. the laser pulse width).

The dependence of onset time for the recorded response on laser radiant exposure validates the assumption that the biophysical mechanism for optical stimulation is rooted in temperature increases at the axonal membrane. Internal conversion and subsequent tissue heating occurs on a femtosecond time scale, which can be considered instantaneous based on the microsecond time scales in the discussion. Accordingly tissue heating occurs as soon as the laser light is deposited in the tissue. As described previously, the temperature increase in nerve tissue (mediating the mechanism of stimulation) is directly proportional to laser radiant exposure, which is delivered uniformly in time by the optical nerve stimulator. Thus, it is expected that if laser radiant exposure used to stimulate the nerve is doubled, the temperature will increase to threshold in half the time and the onset time in the recorded response should occur in half the pulse width of the laser. This effect is clear in FIG. 5. FIG. 5c uses double the radiant exposure used in FIG. 5b, which is slightly above stimulation threshold for this particular nerve (0.5 J/cm2). At stimulation threshold the action potential propagation occurs once all optical energy has been deposited in tissue (as shown in FIG. 4). Conduction velocity of the action potential is constant regardless of laser radiant exposure; consequently the propagation time from stimulus to recording is the same for FIGS. 5b and 5c. With a conduction time for stimulus to recording of about 1.8 msec, the onset of propagation in FIG. 5b occurs at 5.8 msec with a 6 msec laser pulse. Assuming the same conduction time for FIG. 5c, however, the onset of propagation occurs at 2.8 msec. FIG. 5 provides experimental proof that radiant exposures greater than threshold will initiate action potentials before completion of the laser pulse indicating propagation will begin as soon as the temperature rise required for excitation (threshold temperature at the axonal membrane) is reached. Note the probability of stimulation is increased with increasing radiant exposure and more axons are recruited leading to a greater magnitude in the response.

C. Defining the Nature and Magnitude of Thermal Gradient for Optical Stimulation:

Photothermal effects include a large group of interaction types resulting from the transformation of absorbed light energy to heat, leading to a local temperature increase and thus a temperature gradient both in time and in space. It is essential to emphasize that thermal interactions in tissue are typically governed by rate processes, where both the temperature and time are parameters of major importance. Heat flows in biological tissue whenever a temperature difference exists according to the laws of thermodynamics. The primary mechanisms of heat transfer to consider include: conduction, convection, and radiation [32]. This section details and quantifies the spatial and temporal gradients required for optical nerve stimulation.

Figure 6:
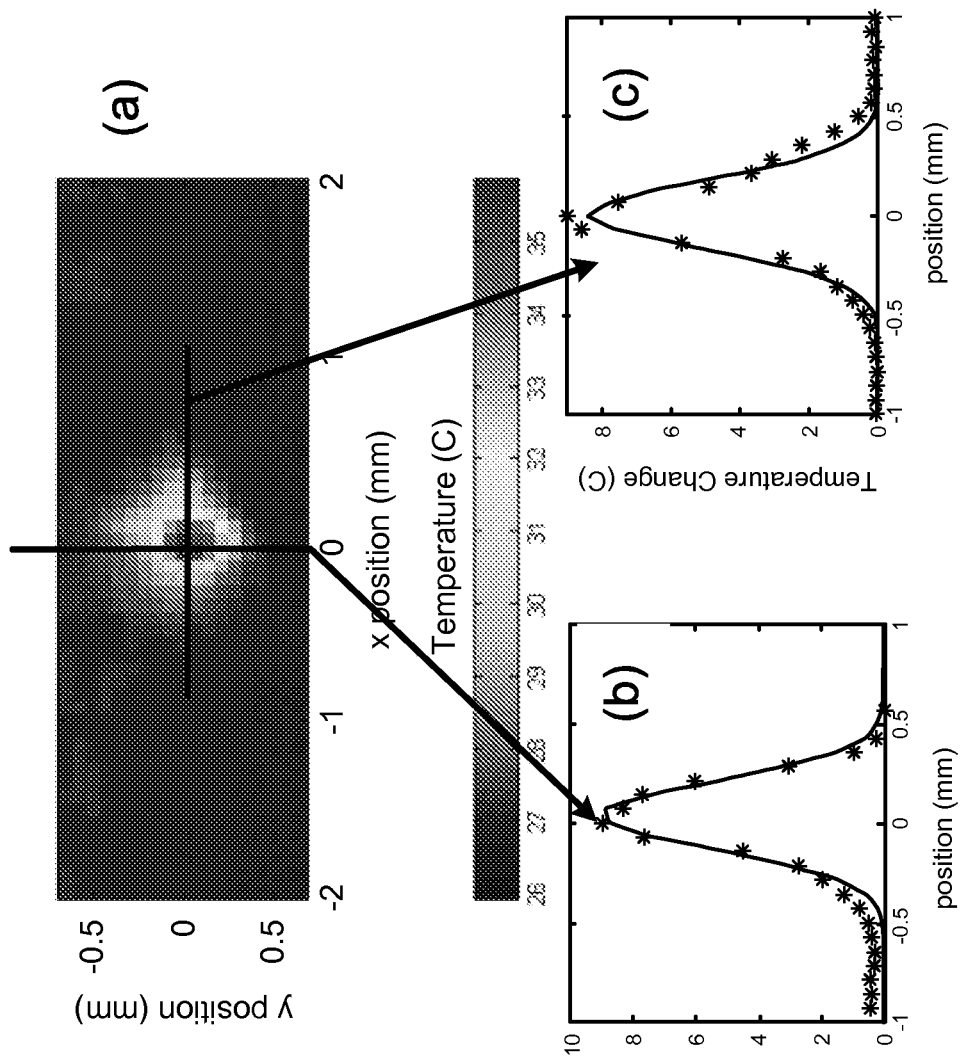
FIG. 6 shows a temperature spatial profile measurement of the nerve surface in vivo using the thermal camera from UT Austin immediately following optical stimulation. Threshold (0.4 J/cm²) radiant exposure with a 600 micron fiber yields a peak tissue temperature=35.86° C., peak temperature rise=8.95° C., and average temperature rise=3.66° C. The calculated Gaussian spot=0.37 mm². The position of the maximum pixel for 0.4 J/cm² stimulation (stars) and Gaussian fit (solid line) of temperature profile for maximum linescan in x and y are below.

The understanding that a thermal gradient in the target nerve is the biophysical mechanism for excitation combined with knowledge of the extent of these temperature rises affords incite into some fundamental limitations and optimal parameters for appropriate use of this technique. First, some conclusions on the spatial selectivity of this technique can be drawn. It is somewhat surprising that the temperature profile follows a Gaussian distribution in space (as shown in FIG. 6) with such a small optical fiber to tissue distance (0.5 mm), since Verdaasdonk and Borst (REF) have shown a more uniform beam shape at this distance. Thus, the spot calculated using the angle of light divergence from the fiber (NA=0.39, divergence=23°) assuming a uniform beam (roughly 1 mm$^2$) is actually a larger estimation than the Gaussian spot size calculated in the example (0.37 mm$^2$). Assuming a specific temperature rise is responsible for action potential generation with pulsed light, the effective stimulation area must occur within a very small spot where the peak temperature change within the tissue is high. It can be inferred from the temperature change versus position graphs in FIG. 6 that near stimulation threshold the effective radius is confined to the tip of the Gaussian curve, on the order of 200 µm or less. This validates the extremely high spatial precision seen with TONS and the technique's ability to excite discrete populations of axons within individual nerve fascicles. Note the optical fiber size used in these experiments has a 600 µm diameter; therefore the affected tissue area is actually smaller than the size of the fiber and obviously significantly smaller than the zone of irradiated tissue if a Gaussian beam profile develops. If the laser energy is increased, a greater tissue radius will overcome the required temperature change threshold. As a result, the selectivity will ultimately decrease as a greater area (thus greater number of axons) will be excited by the incident laser beam. Theoretically, the minimum spot size for optical stimulation is limited only by light diffraction and no doubt can be delivered to tissue via 10 µm optical fibers.

Figure 7:
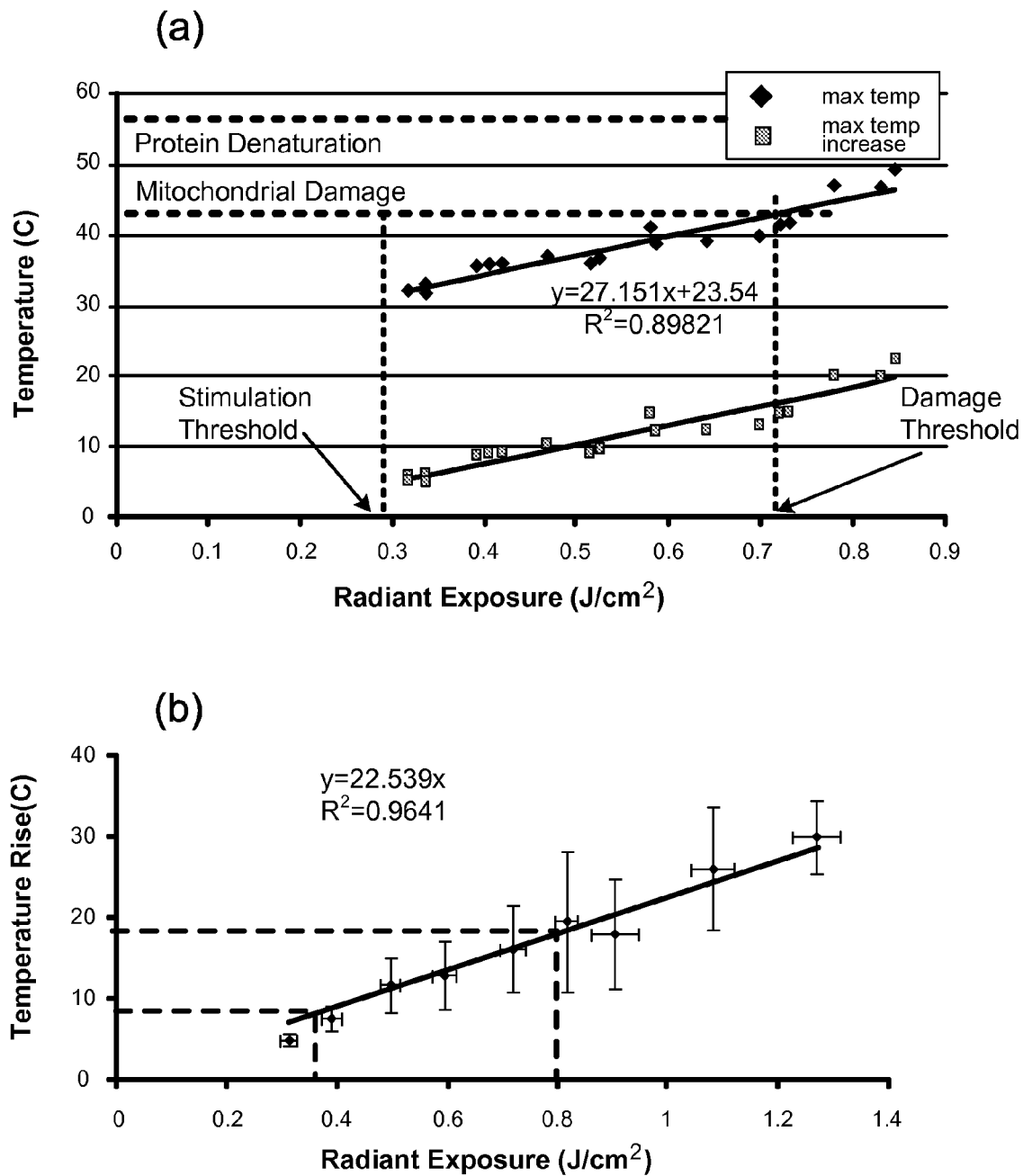
FIG. 7 shows (a) a maximum temperature in hydrated tissue (diamonds) and peak temperature rise in tissue (squares) as a function of radiant exposure immediately following laser stimulation, where stimulation threshold occurs between 0.3-0.4 J/cm², onset of minimal thermal changes in tissue occurs at 43° C., which corresponds to the onset of thermal damage seen in previously published histological analysis (0.8-1.0 J/cm2), and (b) average temperature rise from multiple trials (n=12).

Secondly, an upper limit to the range of non-damaging laser radiant exposures for low frequency optical stimulation is obtained. The literature suggests that thermal changes to mitochondria may begin to occur with temperatures as low as 43° C. [33, 34], while protein denaturation begins at tissue temperatures close to 56-57° C. [17]. As shown in FIG. 7, this temperature corresponds to an onset of thermal changes in peripheral nerve connective tissues with radiant exposures as low as 0.75 J/cm$^2$, while thermal damage to the actual underlying axons will require laser energies greater than this value based on the exponential nature of tissue absorption. These results support the reported tissue damage threshold radiant exposures determined from histological analysis of short term laser nerve stimulation (0.8-1.0 J/cm$^2$) [1]. Owing to the fact that the nerve is exposed through an open incision and hydrated with room temperature saline (baseline temperature=27° C.), the maximum temperature rise at threshold is still below normal body temperature (36° C.) and therefore well below temperatures required for thermal changes or tissue damage. These results imply that optical stimulation of peripheral nerves are mediated through surface thermal gradient of 7-10° C. temperature rises. Furthermore, this phenomenon is theoretically non-damaging in peripheral nerve tissue with radiant exposures at least two times the threshold required for action potential generation.

Finally, the upper limits for repetition rate without leading to superposition of temperature in tissue upon multiple pulses are surmised. One can deduce from FIG. 8 that temperature superposition will begin to occur at higher repetition rates (>4-5 Hz) as the tissue requires slightly greater than 200 msec to return to baseline temperature. At repetition rates greater than 5 Hz, or one pulse every 200 msec, tissue temperatures will become additive with each ensuing laser pulse and resulting tissue damage may begin to occur with long term stimulation. This assumption is supported by the results shown in FIG. 9. With low frequency stimulation (FIG. 9*a*) the resultant heat load in tissue following the laser pulse has adequate time to diffuse out of the irradiated zone via heat conduction. Alternatively, higher frequency stimulation is clearly marked by temperature superposition as additional pulses become additive to the overall tissue temperature. Conduction is overcome by the frequency of laser pulses and within 5 to 10 pulses a steady state temperature and baseline are achieved. According to the results shown in FIG. 6*a* damage will occur with changes between 18 and 20° C. Temperature increases greater than those recorded in the high frequency stimulation experiment are approaching this upper limit using threshold value radiant exposures. FIG. 9*b* plainly shows that the upper limit for the frequency of optical stimulation is 5 Hz.

Photothermal interaction leading to temperature increase is highly dependent on the optical properties of the nerve such as absorption and scattering coefficient and thermal properties such as thermal conductivity and specific heat [35]. In the infrared, the diameter of the sciatic nerve is much larger when compared with the penetration depth of the light stimulus employed. This implies that all light energy that enters the tissue is trapped inside except losses from diffuse reflection. Absorption coefficients are very high compared to the effective scattering in this wavelength range because soft tissue is dominated by forward scattering (g is about 0.9) [36]. Therefore absorption alone is the significant factor for interaction of the laser light with tissue and scattering does not play a significant role in the light distribution and resulting light induced effect on the nervous tissue. To calculate the percentage of surface temperature that reaches the axonal layer in peripheral nerve, Beer's Law is employed and the following assumptions are made: (a) absorption dominated laser penetration ($\mu_a(\lambda)$=3 mm$^{-1}$ for $\lambda$=2.12), (b) peripheral nerve connective tissue (epineurium, perineurium, endoneurium) is a homogenous tissue, (c) the average thickness of the layers surrounding the axonal layer is 150 µm, (d) the minimum surface temperature rise required for optical stimulation is 7-10° C., and (e) the percentage of light attenuation is equal to the percentage of temperature attenuation in a single layered medium. These assumptions predict that 63.8% of the light entering the peripheral nerve surface will remain at the average depth of the axonal layer for selective stimulation of a specific fascicle. Thus, the temperature rise required at the surface of the Schwann cells (myelination) surrounding the axonal membrane to result in optical stimulation of excitable neural tissue is approximately 4.5-6.4° C. All types of neural tissues can be optically stimulated with the use of optimal laser parameters based on tissue structure and morphology. However, it is important to understand that some physical substance (i.e. connective tissue) to hold the thermal gradient drastically decreases the required radiant exposure needed to facilitate neural excitation. Therefore, to selectively excite cultured neurons in a large bath medium may require one of three things: 1) a greater radiant exposure that reported here, 2) an exogenous chromophore, or 3) a specific wavelength targeting substances that lie close to the axonal membrane to establish the necessary thermal gradient and cause the desired stimulatory effect.

D. Possible Physiological Stimulation Mechanisms from a Thermal Gradient:

It is well known in electrical stimulation that membrane depolarization occurs at the cathode where the concentration of negative potential, or charge density, reduces the potential difference across the membrane subsequently activating voltage gated ion channels leading to a transmembrane current from capacitive conductance and action potential propagation [37]. The results presented in the example imply that a temperature rise leading to a thermal gradient is established at the axonal membrane level upon pulsed laser irradiation and provide evidence that this type of microscale thermal interaction is the biophysical mechanism of optical nerve stimulation. Information on the biophysical mechanism now helps guide experimental research in pursuit of a physiological mechanism at the membrane level. The microscopic heating effects taking place at the cellular level, such as the heating of cellular organelles or changing of channel gating kinetics are not verified through these experiments; however, some plausible explanations for this photobiological phenomenon are given.

Temperature can affect action potential propagation in three ways: 1) the Nernst equilibrium potentials are inversely proportional to the absolute temperature, 2) the probability of ion channel opening is temperature dependent, and 3) a change in temperature changes the amplitude and duration of the signal by a common temperature factor governing the rate for channel induction called a Q10 [38]. One potential hypothesis for the physiological mechanism for optical stimulation is the activation of heat sensitive channels, where the gating mechanism is markedly different from the other channel types; voltage gated, ligand gated, and mechanosensitive ion channels. The equilibrium change from closed to open states for all channel types depends on the temperature dependent Gibbs free energy change. A review of the known ion channels gated by heat is given by Cesare, et al [39] who suggests that this temperature rise causes the heat sensitive channels to change to a more disordered state. No accessory proteins or signaling pathway is responsible for the gating of these channels, rather some intrinsic gating unit within the channel [40, 41]. These channels can undergo sensitization which causes a shift in the relationship linking temperature to the probability that a channel is open toward a lower temperature [42]. This may explain the reason a temperature rise and not an absolute temperature is required for activation. The known heat sensitive channels responding to increase in temperature all have extremely large Q(10) values (>10) and include; the TREK-1 potassium channel and 5 cation channels from the transient receptor potential family, vianilloid subfamily [43, 44]. TRPV1, 2, and 3 are highly expressed in the dorsal root ganglia. Of these, the TRPV1 and TRPV3, Specifically, TRPV1 and TRPV3 are the likely candidates for targeted optical stimulation because they open at about 38 degrees C. It is well known that these channels are expressed afferent sensory neurons [45], however recent evidence supports the existence of TRPV1 in efferent fibers [46]. A second hypothesis involves Na channel activation based on a local increase in the probability of channel transition to open resulting from a temperature increase. It is assumed that this is a likely candidate since sodium channels typically initiate the onset and propagation of a potential in a stimulated axon. The Q10 values for these channels are significantly lower than those of the heat sensitive channels, however, with the abundance of sodium channels in the axon together with the temperature increases implicated in this paper from optical stimulation the initiation of a localized sodium current sufficient for stimulation is certainly plausible.

In sum, the results presented in the example reveal that neural activation with pulsed light occurs by a transient thermally mediated mechanism. The electric field effect, photochemical means, and photomechanical mechanisms are discarded as possible means for activation of nerve potentials. Data collected reveal that the spatial and temporal nature of this temperature rise, including a measured surface temperature change required for stimulation of the peripheral nerve (7-10° C.) and at the axon level (4.5-6.4° C.). This information has been used to detail the limits in selectivity, pulse duration, and repetition rate using this technique in the peripheral nerve. Ultimately, it is envisioned that this information will form the basis for the development of a portable, hand-held device for optical stimulation based on solid state diode laser technology, operating at the optimal laser parameters to incite a safe and effective motor response. Such a device would have utility in both basic electrophysiology studies as well as clinical procedures that currently rely on electrical stimulation of neural tissue.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

LIST OF REFERENCES

[1] Wells, J. D., Kao, C., Mariappan, K., Albea, J., Jansen, E. D., Konrad, P., Mahadevan-Jansen, A., *Optical Stimulation of Neural Tissue in vivo*. Optics Letters, 2005. 30(5): p. 504-507.

[2] Wells, J. D., Kao, C., Jansen, E. D., Konrad, P., Mahadevan-Jansen, A., *Application of Infrared Light for in vivo Neural Stimulation*. Journal of Biomedical Optics, 2005. 10: p. 064003.

[3] Jacques, S. L., *Laser-tissue interactions. Photochemical, photothermal, and photomechanical*. Surg Clin North Am, 1992. 72(3): p. 531-58.

[4] Chung, M. K., A. D. Guler, and M. J. Caterina, *Biphasic currents evoked by chemical or thermal activation of the heat-gated ion channel, TRPV3*. J Biol Chem, 2005. 280 (16): p. 15928-41.

[5] Orchardson, R., *The generation of nerve impulses in mammalian axons by changing the concentrations of the normal constituents of extracellular fluid*. J Physiol, 1978. 275: p. 177-89.

[6] Quasthoff, S., *A mechanosensitive K+ channel with fast-gating kinetics on human axons blocked by gadolinium ions*. Neurosci Lett, 1994. 169(1-2): p. 39-42.

[7] Yamamoto, M., et al., *Production of singlet oxygen on irradiation of a photodynamic therapy agent, zinc-coproporphyrin III, with low host toxicity*. Biometals, 2003. 16(4): p. 591-7.

[8] Takahashi, M., et al., *Roles of reactive oxygen species in monocyte activation induced by photochemical reactions during photodynamic therapy*. Front Med Biol Eng, 2002. 11(4): p. 279-94.

[9] Tonita, M. A., R. M. Ion, and B. Carstocea, *Photochemical and photodynamic properties of vitamin B2—ribofiavin and liposomes*. Oftalmologia, 2003. 58(3): p. 29-34.

[10] Conlan, M. J., J. W. Rapley, and C. M. Cobb, *Biostimulation of wound healing by low-energy laser irradiation. A review*. J Clin Periodontol, 1996. 23(5): p. 492-6.

[11] Walsh, L. J., *The current status of low level laser therapy in dentistry. Part 1. Soft tissue applications*. Aust Dent J, 1997. 42(4): p. 247-54.

[12] Boulnois, J. L. and A. Morfino, [*Photo-biomolecular effects of laser radiation*]. Minerva Med, 1983. 74(27): p. 1669-73.

[13] Doukas, A. G., D. J. McAuliffe, and T. J. Flotte, *Biological effects of laser-induced shock waves: structural and functional cell damage in vitro*. Ultrasound Med Biol, 1993. 19(2): p. 137-46.

[14] Doukas, A. G., et al., *Physical factors involved in stress-wave-induced cell injury: the effect of stress gradient*. Ultrasound Med Biol, 1995. 21(7): p. 961-7.

[15] Doukas, A. G. and T. J. Flotte, *Physical characteristics and biological effects of laser-induced stress waves*. Ultrasound Med Biol, 1996. 22(2): p. 151-64.

[16] Jansen, E., *Laser Tissue Interactions*. 1st ed. Encylopedia of Biomaterials and Biomedical Engineering. 2004: Marcel Dekker Publishing. 883-891.

[17] Thomsen, S., *Pathologic analysis of photothermal and photomechanical effects of laser-tissue interactions*. Photochem Photobiol, 1991. 53(6): p. 825-35.

[18] Welch, A. J. and M. van Gemert, *Optical-thermal response of laser irradiated tissue*. Plenum Press, New York, 1995.

[19] Telenkov, S. A., et al., *Differential phase optical coherence probe for depth-resolved detection of photothermal response in tissue*. Phys Med Biol, 2004. 49(1): p. 111-9.

[20] Rylander, C. G., et al., *Quantitative phase-contrast imaging of cells with phase-sensitive optical coherence microscopy*. Opt Lett, 2004. 29(13): p. 1509-11.

[21] Kim, J., et al., *Optical coherence tomography speckle reduction by a partially spatially coherent source*. J Biomed Opt, 2005. 10(6): p. 064034.

[22] Torres, J. H., et al., *Limitations of a thermal camera in measuring surface temperature of laser-irradiated tissues*. Lasers Surg Med, 1990. 10(6): p. 510-23.

[23] Waldman, G., *Introduction to Light: The Physics of Light, Vision, and Color*. 1983, Englewood Liffs, N.J.: Prentice-Hall, Inc.

[24] Niemz, M. H., *Laser-Tissue Interactions*. 3rd ed. 2004: Springer. 308.

[25] Hill, B. C., et al., *Laser interferometer measurement of changes in crayfish axon diameter concurrent with action potential*. Science, 1977. 196(4288): p. 426-8.

[26] Glickman, R., Natarajan, M, Rockwell, B, Denton, M, Maswadi, S, Kumar, N, Nieves-Roldan, F. *Intracellular signaling mechanisms responsive to laser-induced photochemical and thermal stress*. in *Proc. of SPIE*. 2005. Bellingham, Wash.

[27] Hirase, H., et al., *Multiphoton stimulation of neurons*. J Neurobiol, 2002. 51(3): p. 237-47.

[28] Norton, S. J., *Can ultrasound be used to stimulate nerve tissue?* Biomed Eng Online, 2003. 2: p. 6.

[29] Shusterman, V., et al., *Direct mechanical stimulation of brainstem modulates cardiac rhythm and repolarization in humans*. J Electrocardiol, 2002. 35 Suppl: p. 247-56.

[30] Welch, A. J. and M. J. C.v. Gemert, *Optical-thermal response of laser-irradiated tissue*. Lasers, photonics, and electro-optics. 1995, New York: Plenum Press. xxvi, 925 p.

[31] Jansen, E. D., et al., *Laser-tissue interaction during transmyocardial laser revascularization*. Ann Thorac Surg, 1997. 63(3): p. 640-7.

[32] Incropera, F. P., *Fundamentals of Heat and Mass Transfer*. 5th ed. 2002: John Wiley and Sons, Inc.

[33] Borrelli, M. J., et al., *Sensitization to hyperthermia by 3,3'-dipentyloxacarbocyanine iodide: a positive correlation with DNA damage and negative correlations with altered cell morphology, oxygen consumption inhibition, and reduced ATP levels*. Int J Hyperthermia, 1991. 7(2): p. 243-61.

[34] Cole, A. and E. P. Armour, *Ultrastructural study of mitochondrial damage in CHO cells exposed to hyperthermia*. Radiat Res, 1988. 115(3): p. 421-35.

[35] Jacques, S. L. and S. A. Prahl, *Modeling optical and thermal distributions in tissue during laser irradiation*. Lasers Surg Med, 1987. 6(6): p. 494-503.

[36] Jacques S L, A. C., Prahl S A, *Angular dependence of HeNe laser light scattering by human dermis*. Lasers Life Science, 1987. 1: p. 309-334.

[37] Kandel, E. R., J. H. Schwartz, and T. M. Jessell, *Principles of neural science*. 4th ed. 2000, New York: McGraw-Hill, Health Professions Division. xli, 1414 p.

[38] Weiss, T. F., *Cellular biophysics*. 1996, Cambridge, Mass.: MIT Press.

[39] Cesare, P., et al., *Ion channels gated by heat*. Proc Natl Acad Sci USA, 1999. 96(14): p. 7658-63.

[40] Tominaga, M., et al., *The cloned capsaicin receptor integrates multiple pain-producing stimuli*. Neuron, 1998. 21(3): p. 531-43.

[41] Nagy, I. and H. Rang, *Noxious heat activates all capsaicin-sensitive and also a sub-population of capsaicin-insensitive dorsal root ganglion neurons*. Neuroscience, 1999. 88(4): p. 995-7.

[42] Cesare, P. and P. McNaughton, *A novel heat-activated current in nociceptive neurons and its sensitization by bradykinin*. Proc Natl Acad Sci USA, 1996. 93(26): p. 15435-9.

[43] Benham, C. D., M. J. Gunthorpe, and J. B. Davis, *TRPV channels as temperature sensors*. Cell Calcium, 2003. 33(5-6): p. 479-87.

[44] Liman, E. R., *Thermal gating of TRP ion channels: food for thought?* Sci STKE, 2006. 2006(326): p. pe12.

[45] Lyfenko, A., et al., *The effects of excessive heat on heat-activated membrane currents in cultured dorsal root ganglia neurons from neonatal rat*. Pain, 2002. 95(3): p. 207-14.

[46] Van Der Stelt, M. and V. Di Marzo, *Endovanilloids. Putative endogenous ligands of transient receptor potential vanilloid 1 channels*. Eur J Biochem, 2004. 271(10): p. 1827-34.

[47] Hodgkin, A. L. and B. Katz, *The effect of temperature on the electrical activity of the giant axon of the squid*. J Physiol, 1949. 109(1-2): p. 240-9.

[48] Meyer and Hegmann, American Journal of Physiology, 220(5): 1383-7.

[49] Theophilidis and Pavlidou, Muscle & Nerve, 16(1):113-114.

[50] J. M. Khosrofian and B. A. Garetz, Applied Optics, 1983, 22(21): p. 3406-10.

What is claimed is:

1. A method of optically stimulating a neural tissue of a living subject, comprising the steps of:
   (a) introducing at least one of a chromophore and an optical agent to a target neural tissue;
   (b) determining a pulse duration ($T_p$) that is short enough to minimize heat diffusion based on a thermal diffusion time ($T_d$) for the target neural tissue, $T_p < T_d$;
   (c) generating at least one beam of radiation comprising a plurality of pulses with the pulse duration;
   (d) delivering the generated at least one beam of radiation to the target neural tissue; and
   (e) controlling a thermal gradient at the target neural tissue to stimulate the target neural tissue, including
      selecting a wavelength that has minimal absorption in the target neural tissue and optimal absorption in the at least one of a chromophore and an optical agent;

selecting a radiant exposure of the at least one beam of radiation based on a functional relationship between the thermal gradient and a radiant exposure; and selecting the at least one of a chromophore and an optical agent to have predetermined light absorption properties.

2. The method of claim 1, wherein the at least one of a chromophore and an optical agent are introduced to the intracellular space of the target neural tissue, or externally to the neurons of the target neural tissue.

3. The method of claim 1, wherein the at least one beam of radiation has an intensity between a first intensity threshold and a second intensity threshold that is greater than the first intensity threshold, wherein the first intensity threshold is a stimulation threshold of the target tissue, and wherein the second intensity threshold is an ablation threshold of the target tissue.

4. The method of claim 3, wherein the ratio of the second intensity threshold to the first intensity threshold is in a range from 1 to 200.

5. The method of claim 3, wherein the ratio of the second intensity threshold to the first intensity threshold is a function of a wavelength of the at least one beam of radiation.

6. The method of claim 3, wherein the at least one beam of radiation is delivered to the target neural tissue with the radiant exposure no more than 5.0 J/cm².

7. The method of claim 3, wherein the at least one beam of radiation has a wavelength selected such that when delivered to the target neural tissue, it causes a maximal temperature increase and a minimal tissue damage in the target neural tissue.

8. A method of optically stimulating a neural tissue of a living subject, comprising the steps of:
(a) introducing at least one of a chromophores and an optical agents to a target neural tissue;
(b) exposing the target neural tissue to a beam of radiation with a selected radiant exposure for a selected amount of time sufficient to establish a thermal gradient therein and such as to stimulate the target neural tissue, wherein the beam of radiation has an intensity between a stimulation threshold of the target neural tissue and an ablation threshold of the target neural tissue that is greater than the stimulation threshold of the target neural tissue; and
(c) controlling the thermal gradient at the target neural tissue, including
selecting a wavelength that has minimal absorption in the target neural tissue and optimal absorption in the at least one of a chromophore and an optical agent;
selecting a radiant exposure of the at least one beam of radiation based on a functional relationship between the thermal gradient and a radiant exposure; and
selecting the at least one of a chromophore and an optical agent to have predetermined light absorption properties.

9. The method of claim 8, wherein the beam of radiation has a wavelength selected such that when delivered to the target neural tissue, it causes a maximal temperature increase and a minimal tissue damage in the target neural tissue.

10. The method of claim 8, wherein the target neural tissue is characterized with a thermal diffusion time, $T_d$, and wherein the beam of radiation comprises a plurality of pulses with a pulse duration, $T_p$, such that $T_p<T_d$.

11. A method of optically stimulating a neural tissue of a living subject, wherein the neural tissue of interest is characterized with a thermal diffusion time, $T_d$, comprising:
delivering optical energy to a target neural tissues in pulses with a pulse duration $T_p$ such that $T_p<T_d$, and wherein the optical energy is delivered with a radiant exposure that causes a thermal gradient in the target neural tissue, thereby stimulating the target neural tissue; and
controlling the thermal gradient at the target neural tissue, including
selecting a wavelength that has minimal absorption in the target neural tissue and optimal absorption in at least one of a chromophore and an optical agent at the target neural tissue;
selecting a radiant exposure of the optical energy based on a functional relationship between the thermal gradient and a radiant exposure; and
selecting the at least one of a chromophore and an optical agent to have predetermined light absorption properties.

12. The method of claim 11, wherein the introducing the at least one of a chromophore and an optical agent to a target neural tissue comprises introducing the at least one of a chromophore and an optical agent to the target neural tissue prior to the delivering step.

13. The method of claim 11, wherein the delivering step comprises the step of focusing the optical energy on the target neural tissue so that the target neural tissue propagates an electrical impulse.

14. The method of claim 11, wherein the target neural tissue receives the optical energy for an amount of time sufficient to initiate action potential propagation within the target neural tissue.

15. A method of optically stimulating a neural tissue of a living subject, comprising:
(a) introducing at least one of a chromophore and an optical agent to a target neural tissue, wherein the target neural tissue is characterized by a thermal diffusion time, $T_d$ that is predetermined or measured;
(b) determining a pulse duration ($T_p$) that is short enough to minimize heat diffusion based on thermal diffusion time ($T_d$) for the target neural tissue, $T_p<T_d$;
(c) generating at least one beam of radiation comprising a plurality of pulses with the pulse duration;
(d) delivering the generated at least one beam of radiation to the target neural tissue, wherein the at least one beam of radiation is delivered with a radiant exposure selected such as to establish a thermal gradient in the target neural tissue and stimulate the target neural tissue, wherein the radiant exposure is in a range of about 0.3 J/cm² to about 1.0 J/cm²;
(e) controlling the thermal gradient at the target neural tissue, including
selecting a wavelength that has minimal absorption in the target neural tissue and optimal absorption in the at least one of a chromophore and an optical agent;
selecting a radiant exposure of the at least one beam of radiation based on a functional relationship between the thermal gradient and a radiant exposure; and
selecting the at least one of a chromophore and an optical agent to have predetermined light absorption properties.

16. A method of optically stimulating a neural tissue of a living subject, comprising:
(a) introducing at least one of a chromophore and an optical agent to a target neural tissue;
(b) exposing the target neural tissue to a beam of radiation with a selected radiant exposure for a selected amount of time sufficient to establish a thermal gradient therein and such as to stimulate the target neural tissue, wherein the beam of radiation has an intensity between a stimulation threshold of the target neural tissue and an ablation threshold of the target neural tissue that is greater than the stimulation threshold of the target neural tissue, wherein the selected radiant exposure is in a range of about 0.3 J/cm² to about 1.0 J/cm² and the selected amount of time is short enough to minimize heat diffusion based on a thermal diffusion time for the target neural tissue; and (c) controlling the thermal gradient at the target neural tissue, including selecting a wavelength that has minimal absorption in the target neural tissue and optimal absorption in the at least one of a chromophore and an optical agent;

selecting a radiant exposure of the at least one beam of radiation based on a functional relationship between the thermal gradient and a laser radiant exposure; and selecting the at least one of a chromophore and an optical agent to have predetermined light absorption properties.

\* \* \* \* \*